United States Patent
Wong et al.

(10) Patent No.: US 10,023,903 B2
(45) Date of Patent: Jul. 17, 2018

(54) SALIVA COLLECTION, PROCESSING, STABILIZATION, AND STORAGE METHOD

(75) Inventors: David T. Wong, Beverly Hills, CA (US); Wei Liao, North Hills, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 821 days.

(21) Appl. No.: 14/236,963

(22) PCT Filed: Aug. 6, 2012

(86) PCT No.: PCT/US2012/049776
§ 371 (c)(1),
(2), (4) Date: Jun. 23, 2014

(87) PCT Pub. No.: WO2013/020137
PCT Pub. Date: Feb. 7, 2013

(65) Prior Publication Data
US 2014/0329705 A1 Nov. 6, 2014

Related U.S. Application Data

(60) Provisional application No. 61/515,169, filed on Aug. 4, 2011.

(51) Int. Cl.
*C12Q 1/68* (2018.01)
*G01N 1/40* (2006.01)
*G01N 33/53* (2006.01)
*A61B 10/00* (2006.01)
*C12Q 1/6806* (2018.01)

(52) U.S. Cl.
CPC ........ *C12Q 1/6806* (2013.01); *A61B 10/0051* (2013.01); *C12Q 1/68* (2013.01); *G01N 1/4005* (2013.01); *G01N 33/5306* (2013.01); *Y10T 436/2525* (2015.01)

(58) Field of Classification Search
None
See application file for complete search history.

(56) References Cited

U.S. PATENT DOCUMENTS

| 2004/0115692 A1* | 6/2004 | Linder | C12Q 1/6841 435/6.16 |
| 2010/0173295 A1* | 7/2010 | Lenz | G01N 1/30 435/6.11 |
| 2012/0052572 A1* | 3/2012 | Whitney | C12Q 1/6806 435/372 |
| 2013/0209997 A1* | 8/2013 | Whitney | C12Q 1/6806 435/6.1 |

OTHER PUBLICATIONS

Jiang J, Park NJ, Hu S, Wong DT. A universal pre-analytic solution for concurrent stabilization of salivary proteins, RNA and DNA at ambient temperature. Arch Oral Biol. Mar. 2009; 54(3):268-73. Epub Nov. 28, 2008.*
Barnes I, Holton J, Vaira D, Spigelman M, Thomas MG. An assessment of the long-term preservation of the DNA of a bacterial pathogen in ethanol-preserved archival material. J Pathol. Dec. 2000; 192(4):554-9. (Year: 2000).*
Jiang et al., "A universal pre-analytic solution for concurrent stabilization of salivary protein, RNA and DNA at ambient temperature." Archives of Oral Biology, 54(3): 268-273. (2009).
Gekko and Timasheff, "Thermodynamic and kinetic examination of protein stabilization by glycerol." *Biochemistry* 20:4677 (1981).
Lee and Wong, "Saliva: An emerging biofluid for early detection of diseases." *Am J. Dent.* 22:241-8 (2009).
Xiao and Wong, "Method development for proteome stabilization in human saliva." Analytical Chimica Acta, 722: 63-69 (Feb. 19, 2012).
Yan et al., "Systematic comparison of the human saliva and plasma proteomes." *Proteomics Clin. Appl.* 3:116 (2009).
Li et al, "RNA Profiling of Cell-free Saliva Using Microarray Technology." *J. Dent. Res.* 83:199-203 (2004).
Park et al., "Characterization of RNA in Saliva." *Clin. Chem* 52:988-94 (2006).
Park et al. "Characterization of salivary RNA by cDNA library analysis." *Arch. Oral. Biol.*, 52:30-5 (2007).
Hu et al., "Human body fluid proteome analysis." *Proteomics* 6:6326 (2006).
Xiao and Wong, "Proteomics and its applications for biomarker discovery in human saliva." *Bioinformation* 5:294 (Jan. 6, 2011).
Zhang et al, "Salivary Biomarkers for Clinical Applications." *Mol. Diagn. Ther.* 13:245 (2009).
Navazesh M, "Methods for Collecting Saliva." *Ann. NY Acad. Sci* 694: 72-7 (1993).
Li et al. "Salivary Transcriptome Diagnostics for Oral Cancer Detection." *Clin. Cancer Res.* 10:8442-50 (2004).
Martin et al. "A Need for Basic Research on Fluid-Based Early Detection Biomarkers." *Cancer Res.* 70:5203-6 (2010).
Skog et al, "Glioblastoma microvesicles transport RNA and proteins that promote tumour growth and provide diagnostic biomarkers." *Nat. Cell Biol.* 10:1470 (2008).
Deutsch et al. "An approach to remove alpha amylase for proteomic analysis of low abundance biomarkers in human saliva." *Electrophoresis* 29:4150 (2008).
Zhang et al, "Discovery and Preclinical Validation of Salivary Transcriptomic and Proteomic Biomarkers for the Non-Invasive Detection of Breast Cancer." *PloS ONE* 5:e15573 (2010).

(Continued)

*Primary Examiner* — Samuel C Woolwine
*Assistant Examiner* — Olayinka A Oyeyemi
(74) *Attorney, Agent, or Firm* — Riverside Law LLP

(57) ABSTRACT

Provided herein is an all-in-one saliva collection apparatus that collects saliva to allow for the filtration of saliva in order to separate saliva components, such as extracellular proteins and nucleic acids that are not present in intact cells, from the intact cells and debris remaining in the extracted sample. The filtered saliva samples can be aliquoted into two fractions for protein and/or nucleic acid analysis. The present invention further describes long term storage at ambient temperatures of filtered salivary nucleic acids, and long term storage at ambient temperatures of filtered salivary proteins added to an ethanol solution. The filtered cell-free saliva samples have diagnostic usefulness.

23 Claims, 15 Drawing Sheets

(56) References Cited

OTHER PUBLICATIONS

Chevalier et al, "Proteomic Studies of Saliva: A Proposal for a Standardized Handling of Clinical Samples." *Clin. Proteomics* 3:13 (2007).
Palanisamy et al., "AUF1 and HuR Proteins Stabilize Interleukin-8 mRNA in Human Saliva." *J. Dent. Res.* 87:772 (2008).
Michael et al, "Exosomes from human saliva as a source of microRNA biomarkers." *Oral Dis.* 16:34 (2010).
Jiang et al., "Increased Mitochondrial DNA Content in Saliva Associated with Head and Neck Cancer." *Clin. Cancer Res.* 11:2486 (2005).
Sugimoto et al., "Capillary electrophoresis mass spectrometry-based saliva metabolomics identified oral, breast and pancreatic cancer-specific profiles." *Metabolomics* 6:78 (2010).
Xie et al., "Proteomics Analysis of Cells in Whole Saliva from Oral Cancer Patients via Value-added Three-dimensional Peptide Fractionation and Tandem Mass Spectrometry." *Mol. Cell. Proteomics* 7:486 (2008).
Ryu et al., "Oral environmental factors affecting number of microbes in saliva of complete denture wearers." *J. Oral Rehabil.* 37:194 (2010).
Polson et al, "Optimization of protein precipitation based upon effectiveness of protein removal and ionization effect in liquid chromatography—tandem mass spectrometry." *Anal. Technol. Biomed. Life Sci.* 785:263 (2003).

\* cited by examiner

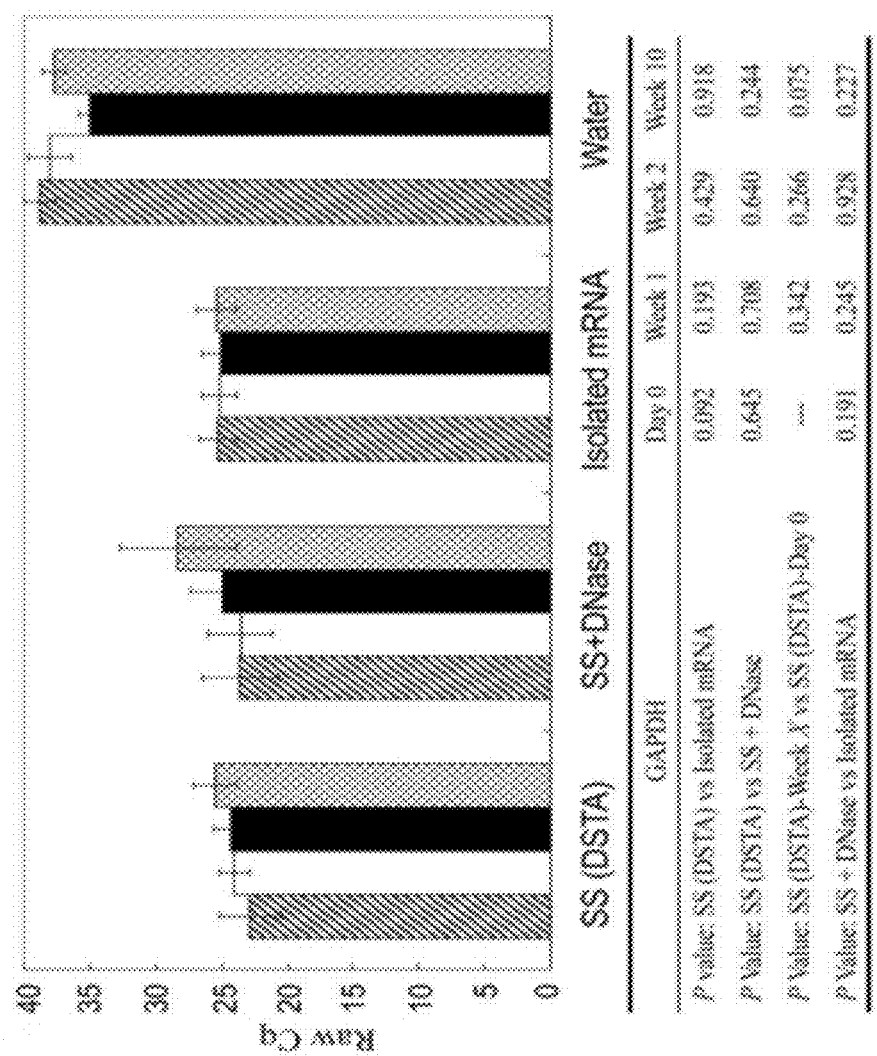
Replacement Sheet
Figure 4A

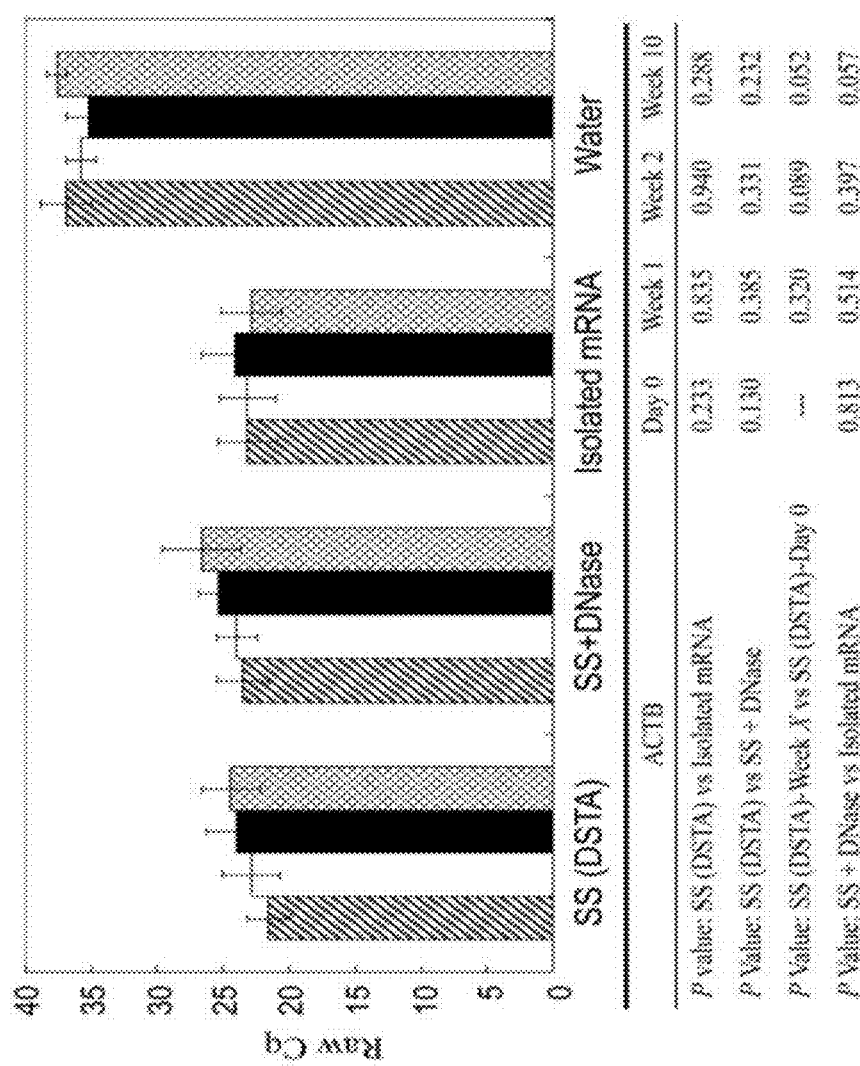
Replacement Sheet
Figure 4B

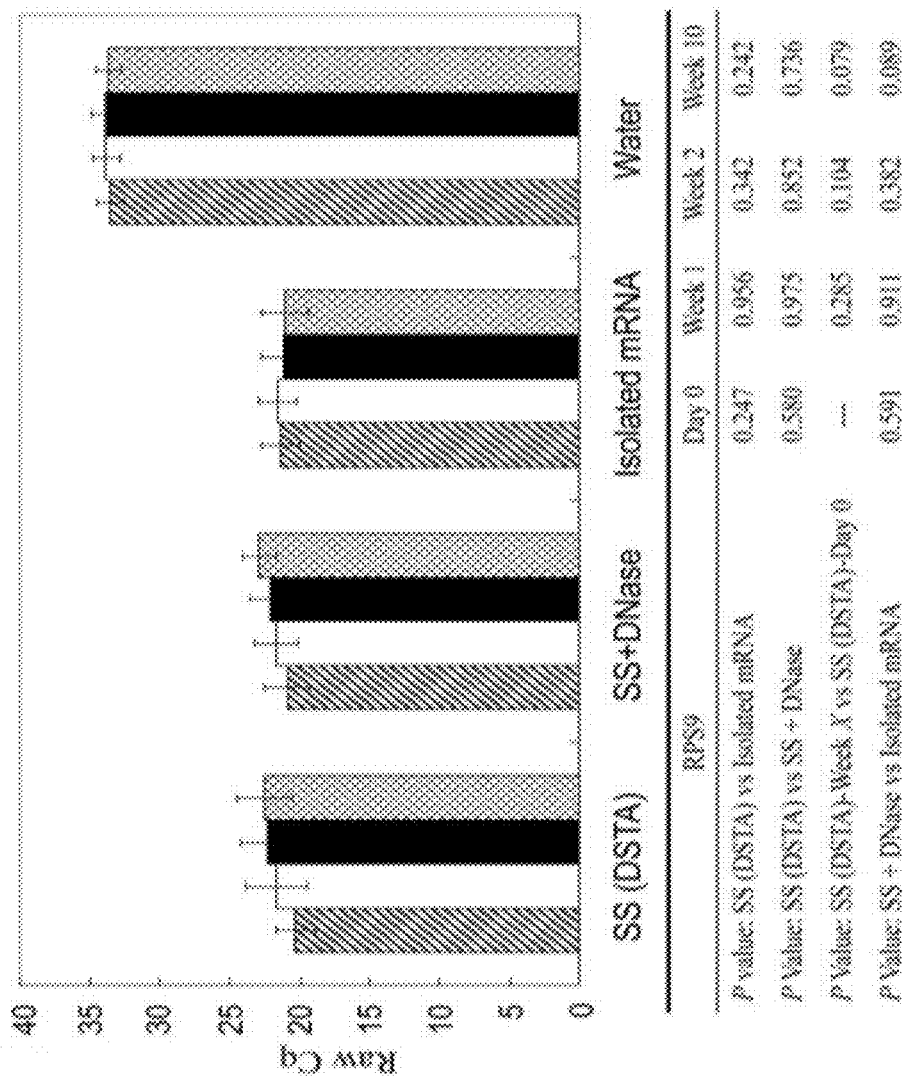
Replacement Sheet
Figure 4C

SALIVA COLLECTION, PROCESSING, STABILIZATION, AND STORAGE METHOD

CROSS-REFERENCES TO RELATED APPLICATIONS

The present application is a 371 U.S. National Phase application of PCT/US2012/049776 which claims priority to U.S. Ser. No. 61/515,169, filed Aug. 4, 2012, herein incorporated by reference in its entirety.

STATEMENT OF GOVERNMENT RIGHTS

This invention was made with Government support under Grant No. CA126733 awarded by the National Institutes of Health. The Government has certain rights in the invention.

FIELD OF THE DISCLOSURE

The present disclosure relates to an apparatus and methods for the analysis of protein and nucleic acids present in cell-free samples of saliva.

BACKGROUND OF THE INVENTION

Interest in using saliva as a diagnostic tool for disease detection and health surveillance is increasing due to its noninvasive accessibility, cost-effectiveness, easy sample collection and processing, and accumulating scientific rationale (Yan et al., *Proteomics Clin. Appl.* 3:116 (2009); Lee and Wong, *Am J. Dent.* 22:241-8 (2009)). Saliva has been used to detect, for example, caries risk, peridontitis, oral cancer, breast cancer, lung cancer, Sjögren's syndrome, salivary gland disease and infectious diseases such as hepatitis, HIV, and HCV. Saliva is therefore an attractive diagnostic sample alternative for blood, serum, or plasma.

Saliva is ideal for nucleic acid analysis. The human salivary transcriptome in cell-free saliva was first discovered in 2004 by use of microarray technology (Li et al, *J. Dent. Res.* 83:199-203 (2004)). Investigations into the characteristics of salivary RNA followed, which led to the development of salivary transcriptomics as a research focus. (Park et al., *Clin. Chem* 52:988-94 (2006); Park et al. *Arch. Oral. Biol.*, 52:30-5 (2007)).

Saliva is additionally ideal for proteomic analysis. Profiling proteins in saliva over the course of disease progression can reveal biomarkers indicative of different stages of diseases, which can be useful in early detection and/or medical diagnosis (Hu et al., *Proteomics* 6:6326 (2006)). Proteomics is widely envisioned as a unique and powerful approach to biomarker development. As proteomic technologies continue to mature, proteomics has the great potential for salivary proteomic biomarker development and further clinical applications (Xiao and Wong, *Bioinformation* 5:294 (2011); Zhang et al, *Mol. Diagn. Ther.* 13:245 (2009)).

However, current methods for the extraction of nucleic acids and protein from saliva require the saliva sample to be processed immediately after collection requiring special instrumentation and trained personnel. For example, current standard procedures for salivary transcriptomic diagnostics require mRNA isolation, which is time-consuming and labor-intensive. In addition, operator differences increase as procedural complexity increases. Although several automated devices are commercially available to enhance mRNA isolation efficiency (e.g., KING FISHER<QIACUBE, and MAXWELL 16), throughput is still limited by the number of samples processed per run. Furthermore, particular care is required when working with RNA because of its inherent instability and the ubiquitous presence of RNases. Likewise, current standard procedures for salivary proteomic diagnostics require the addition of protease inhibitors to prevent proteolysis. As a result, current methods for transcriptomic and proteomic diagnostics require the addition of nucleic acid and protein stabilizers to be added to saliva samples followed by storage at −80° C.

The ability to analyze saliva to monitor health and disease is a highly desirable goal for oral health promotion and research. In order to fully realize the diagnostic and research uses of saliva as a source of biomarkers, systems for collection, handling, and room-temperature storage of saliva by non-professionals in a user friendly integrated point-of-care collection system are desirable.

BRIEF SUMMARY OF THE INVENTION

Saliva is an ideal translational research tool and diagnostic medium and is being used in unique ways to provide molecular biomarkers for a variety of oral and systemic diseases and conditions. The ability to analyze saliva to monitor health and disease is highly desirable for oral health promotion and research. Saliva has been used to detect caries risk, periodontitis, oral cancer, breast cancer, salivary gland disease, and infectious diseases such as hepatitis, HIV, and HCV. Measurement of salivary analytes requires optimal collection, processing and storage procedures and conditions.

In an embodiment, a method for stabilizing RNA and protein samples isolated from a saliva sample is provided. The method includes a) collecting a saliva sample from a subject; b) filtering the saliva sample to produce a filtered sample that is free of cells; c) collecting the filtered sample in at least a first and a second receiving device; d) adding an alcohol solution to the first receiving device to produce an alcohol-containing filtered sample comprising a protein sample, with the proviso that alcohol is not added to the second receiving device to produce an alcohol-free filtered sample comprising a nucleic acid sample; wherein the protein sample and the nucleic acid sample are stabilized for at least 3 days when stored at 25 degrees Celsius; and e) performing an analysis on the filtered sample collected in the first and second receiving devices comprising one or more of: a protein analysis on the alcohol-containing filtered sample or a nucleic acid analysis on the alcohol-free filtered sample. In a further embodiment, in accordance with any of the above embodiments or in combination with any of the above embodiments, the nucleic acid is DNA. In a further embodiment, in accordance with any of the above embodiments or in combination with any of the above embodiments, the nucleic acid analysis is polymerase chain reaction (PCR). In a further embodiment, in accordance with any of the above embodiments or in combination with any of the above embodiments, the nucleic acid is RNA. In a further embodiment, in accordance with any of the above embodiments or in combination with any of the above embodiments, the nucleic acid analysis is RT-PCR. In a further embodiment, in accordance with any of the above embodiments or in combination with any of the above embodiments, the RT-PCR is reverse transcription quantitative real-time PCR (RT-qPCR). In a further embodiment, in accordance with any of the above embodiments or in combination with any of the above embodiments, the ethanol solution comprises 20% ethanol. In a further embodiment, in accordance with any of the above embodiments or in combination with any of the above embodiments, the ethanol solution comprises 15-25% ethanol. In a further embodiment, in accordance with any of the above embodiments or in combination with any of the above embodiments, the ethanol solution comprises 5-35% ethanol. In a further embodiment, in accordance with any of the above embodiments or in combination with any of the above embodiments, the protein analysis comprises western blot, mass spectrometry protein identification, or ELISA. In a further embodiment, in accordance with any of the above embodiments or in combination with any of the above embodiments, the filtered sample is stored at ambient temperature. In a further embodiment, in accordance with any of the above embodiments or in combination with any of the above embodiments, the filtered sample is stored at ambient temperature for at least two weeks without more than 50% degradation of proteins or nucleic acids present in the filtered sample. In a further embodiment, in accordance with any of the above embodiments or in combination with any of the above embodiments, the filtered sample is stored at ambient temperature for at least two weeks without more than 25% degradation of proteins or nucleic acids present in the filtered sample. In a further embodiment, in accordance with any of the above embodiments or in combination with any of the above embodiments, the filtered sample is stored at ambient temperature for at least ten weeks without more than 50% degradation of proteins or nucleic acids present in the filtered sample. In a further embodiment, in accordance with any of the above embodiments or in combination with any of the above embodiments, the filtered sample is stored at ambient temperature for at least ten weeks without more than 25% degradation of proteins or nucleic acids present in the filtered sample. In a further embodiment, in accordance with any of the above embodiments or in combination with any of the above embodiments, the filter is selected from the group consisting of a 0.22 µm, 0.45 µm and 5.0 µm hydrophilic membrane. In a further embodiment, in accordance with any of the above embodiments or in combination with any of the above embodiments, the filter is a 0.22 µm hydrophilic membrane.

In another embodiment, an apparatus for the collection of saliva samples for biomarker detection is provided. In a further embodiment, in accordance with any of the above embodiments or in combination with any of the above embodiments, the apparatus comprises a sample collection pad, a filter, two or more receiving devices, wherein the receiving devices are selected from an mRNA collection tube, a polypeptide collection tube, and a DNA collection tube, wherein the polypeptide collection tube comprises an ethanol solution, and the DNA collection tube comprises a DNA stabilizer, wherein the filter is operably connected to the receiving devices. In a further embodiment, in accordance with any of the above embodiments or in combination with any of the above embodiments, the filter is selected from the group consisting of a 0.22 µm, 0.45 µm or 5.0 µm hydrophilic membrane. In a further embodiment, in accordance with any of the above embodiments or in combination with any of the above embodiments, the filter is a 0.22 µm hydrophilic membrane. In a further embodiment, in accordance with any of the above embodiments or in combination with any of the above embodiments, a method of using the apparatus is provided. The method includes inserting the sample collection pad into the oral cavity for sufficient time to moisten the sample collection pad, inserting the collection pad into the receiving tube, applying sufficient force to cause the materials collected in the collection pad to pass through the filter thereby forming a filtered sample, and collecting the filtered sample into one or more receiving devices.

In another embodiment, a method for stabilizing RNA and protein samples isolated from a saliva sample is provided. The method includes a) collecting a saliva sample from a human subject; b) filtering the saliva sample using a 0.22 µm to 5.0 µm hydrophilic membrane to produce a filtered sample that is free of cells; c) collecting the filtered sample in at first and a second receiving device; d) adding an ethanol solution to the first receiving device to produce a 20% ethanol-containing filtered sample comprising a protein sample, with the proviso that alcohol is not added to the second receiving device to produce an alcohol-free filtered sample comprising a nucleic acid sample; wherein the protein sample and the nucleic acid sample are stabilized for at least 3 days when stored at 25 degrees Celsius. In a further embodiment, in accordance with any of the above embodiments or in combination with any of the above embodiments, the method further comprises the step of (e) performing an analysis on the filtered samples collected in the first and second receiving devices comprising one or more of: a protein analysis on the ethanol-containing filtered sample or a nucleic acid analysis on the alcohol-free filtered sample. In a further embodiment, in accordance with any of the above embodiments or in combination with any of the above embodiments, the protein sample is stabilized for at least 2 weeks when stored at 25 degrees Celsius. In a further embodiment, in accordance with any of the above embodiments or in combination with any of the above embodiments, the nucleic acid sample is stabilized for at least 10 weeks when stored at 25 degrees Celsius. In some embodiments, the ethanol solution comprises 15-25% ethanol. In a further embodiment, in accordance with any of the above embodiments or in combination with any of the above embodiments, the ethanol solution comprises 5-35% ethanol. In a further embodiment, in accordance with any of the above embodiments or in combination with any of the above embodiments, the hydrophilic membrane in 0.22 µm.

BRIEF DESCRIPTION OF THE DRAWINGS

FIG. 4 illustrates expression levels of 3 SIRG mRNAs measure during 10 weeks of storage at ambient temperature without stabilizing reagent.

DETAILED DESCRIPTION OF THE INVENTION

Introduction

Figure 1:
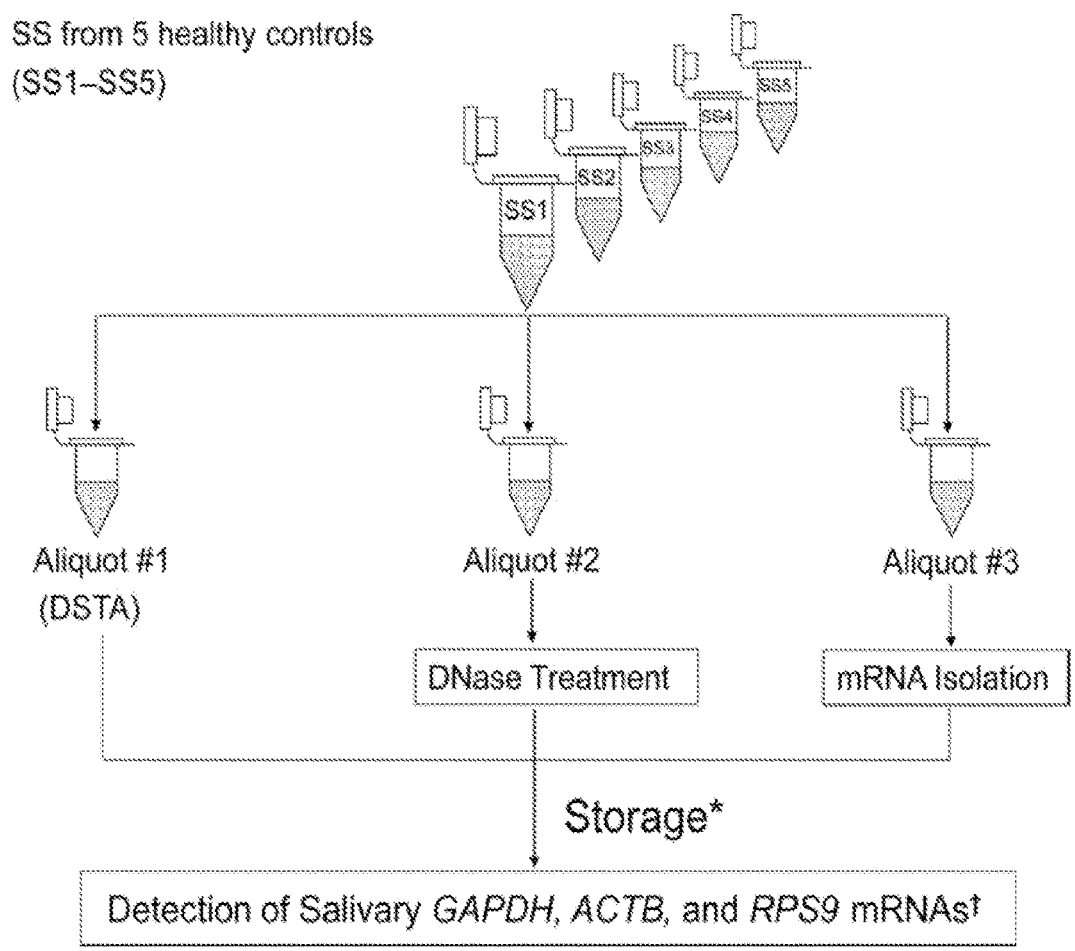
FIG. 1 illustrates a schematic diagram of the experimental design of Example 1.

Human saliva contains an array of analytes (proteins, mRNA, and DNA) that can be used as biomarkers for translational and clinical applications. For example, saliva can be used to detect, caries risk, peridontitis, oral cancer, breast cancer, lung cancer, Sjögren's syndrome, salivary gland disease and infectious diseases such as hepatitis, HIV, and HCV.

A value of using saliva as a source of biomarkers is the ease of sampling and high subject compliance for sample collection. Presence of RNAs and protein in the cell-free fluid phase portion of saliva was confirmed by the procedures described extensively in the Examples. However, current methods for the extraction of nucleic acids and protein from saliva require the saliva sample to be processed immediately after collection using special instrumentation and trained personnel, the addition of nucleic acid and protein stabilizers, and storage at −80° C.

The ability to provide a user friendly and easy to use collector apparatus for major salivary diagnostic analytes is of interest. The present invention provides methods and an apparatus for the collection of saliva and saliva biomarkers. The methods can be carried out by non-professionals in a user friendly integrated point-of-care collection system that allows storage and shipment at room temperature without the addition of commonly used nucleic acid and protein stabilizers.

Definitions

Unless otherwise noted, the technical terms used herein are according to conventional usage as understood by persons skilled in the art. Definitions of common terms in molecular biology may be found in standard texts (e.g. Benjamin Lewin, Genes V, published by Oxford University Press, 1994 (ISBN 0-19854287-9); Kendrew et al. (eds.), The Encyclopedia of Molecular Biology, published by Blackwell Science Ltd, 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8)).

A "saliva sample" refers to samples derived from saliva from an animal that produces saliva. Saliva is a component of oral fluid produced in most animals.

A "filtered sample" refers to a saliva sample that has been processed to remove cells by separating the cell-phase and the fluid phase of saliva. A filtered sample can have more than 50%, more than 75%, more than 95%, or a 100% removal of cells. A sample is filtered to avoid mechanical rupture of cellular elements that could contribute to the detection of unwanted analytes in the cell-free phase. A filtered sample can further exclude extraneous substances, including but not limited to, food debris.

The term "alcohol solution" refers to any solution containing an alcohol such as methanol, isopropyl alcohol, and ethanol. An alcohol solution can contain, for example, 5%, 10%, 20%, 30%, 40%, 50%, 60%, 70%, 80%, 90%, 95%, 96%, 97%, 98%, or 100% alcohol, e.g., ethanol. The term "alcohol-containing filtered sample" refers to a cell free saliva sample comprising an alcohol, e.g., an ethanol solution, as described herein.

The term "alcohol-free filtered sample" refers to a cell free saliva sample that is at least 50%, 60%, 70%, 75%, 80%, 85%, 90%, 95%, 96%, 97%, 98%, 99% or 100% free of alcohol, including but not limited to, isopropyl alcohol, methanol, or ethanol.

The term "analysis" as used herein refers to any quantitative or qualitative examination or measurement of saliva components. Non-limiting examples are analyses that determine the presence or absence of nucleic acids or proteins; over or under expression of nucleic acids or proteins; or a genomic, transcriptomic, or proteomic examination of a saliva sample.

The term "collection apparatus" refers to any apparatus that can be used to collect saliva. As used herein, a collection apparatus includes a sample collection pad as described herein, a filter that is capable of separating cells from a sample as described herein, and a receiving device that is capable of receiving the filtered sample as described herein.

The term "collection pad" refers to any material that is suitable for collection of saliva. Examples can include, but are not limited to, nitrocellulose, cellulose acetate, polyethersulfur fabric, cellulose fiber such as paper strips or cotton, nylon, gel foam, fiber glass, polycarbonate, polyproplene, acetate, rayon, polyester absorbent pad, or other synthetic materials capable of collecting saliva.

The term "filter" refers to any filter capable of separating cells from a saliva sample. Exemplary filters can include, but are not limited to, cellulose fiber matrix, hydrophilic filters, such as those based on polyvinylidene fluoride membrane, or filters based on polypropylene membrane. Filters can have micropores that are a wide variety of sizes, including, but not limited to, 0.22 µm, 0.45 µm and 5.0 µm. The term "filtering" refers to the application of a liquid sample containing cells, e.g. a saliva sample, to a membrane filter. Filtering is the process of removing cells and/or parts of cells from excess fluid in a liquid sample by passing the sample through a microporous membrane filter.

The phrase "free of cells" refers to a sample solution that has been filtered in accordance with the methods of the present invention such that the sample solution is completely or substantially cell-free.

The term "degradation" refers to, for example, the proteolytic cleavage of proteins into smaller peptides and amino acids; or the catalysis of nucleic acids into smaller components. Degradation as used herein results in proteins and nucleic acids having compromised gene expression and clinical utilities.

The term "receiving device" refers to any device capable of collecting a filtered sample. Receiving devices can include, but are not limited to, devices formed wholly or partially from plastic, such as polypropylene, polystyrene, polycarbonate, polyurethane, or polyethylene, polycarbonate, polytetrafluoroethylene, enamel, nylon, ceramic or any combination thereof, or from glass and/or metallic materials. Receiving devices can be, for example, snap cap, screw cap, and loop-cap microcentrifuge tubes.

The term "ambient temperature" is the temperature of the surrounding environment, which generally refers to room temperature in a clinical setting. Ambient temperature is generally between 20 and 25 degrees Celsius.

The term "extracellular" as used herein refers to fluidic space outside the plasma membranes of cells. The composition of the extracellular space can include proteins, nucleic acids, lipids, hormones, microbial product, etc.

The term "stabilizing" or "stabilization" refers to any effect of the methods according to the present invention resulting in the stabilization of the structure and/or activity of a biomolecule, the elongation of the shelf-life of a biomolecule and/or the protection of a biomolecule against stress. This results in a biological activity of the biomolecule which is retained to a significant degree. Exemplary stabilizations can be nucleic acids or proteins that are stabilized for 2 to 10 weeks or more at room temperature.

The term "nucleic acid" refers to deoxyribonucleotides or ribonucleotides and polymers thereof in either single- or double-stranded form, and complements thereof. The term refers to all forms of nucleic acids (e.g., gene, pre-mRNA, mRNA) and their polymorphic variants, alleles, mutants, and interspecies homologs. The term nucleic acid is used interchangeably with gene, cDNA, mRNA, oligonucleotide, and polynucleotide. The term encompasses nucleic acids that are naturally occurring or recombinant. Nucleic acids can (1) code for an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a referenced nucleic acid or an amino acid sequence described herein; (2) specifically bind to antibodies, e.g., polyclonal antibodies, raised against an immunogen comprising a referenced amino acid sequence, immunogenic fragments thereof, and conservatively modified variants thereof; (3) specifically hybridize under stringent hybridization conditions to a nucleic acid encoding a referenced amino acid sequence, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a reference nucleic acid sequence.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The phrase "specifically (or selectively) binds" when referring to a protein, nucleic acid, antibody, or small molecule compound refers to a binding reaction that is determinative of the presence of the protein or nucleic acid, such as the differentially expressed genes of the present invention, often in a heterogeneous population of proteins or nucleic acids and other biologics. In the case of antibodies, under designated immunoassay conditions, a specified antibody may bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity).

Nucleic Acid Analysis

Embodiments described herein include a streamlined, ambient-temperature processing, stabilization, and storage of nucleic acids derived from saliva. Direct saliva transcriptome and genome analyses using cell-free saliva supernatant instead of isolated nucleic acids, which include the processing, stabilization, and storage of saliva samples, as described herein, can be performed at ambient temperature without stabilization agents. In some embodiments, stabilization agents can be included. In some embodiments, alcohol can be included.

Profiling salivary nucleic acids over the course of disease progression can reveal potential biomarkers indicative of different stages of disease, which can be useful in early detection of disease. Nucleic acid stabilization requiring extremely low temperatures or nucleic acid stabilization chemicals can be impractical for field applications or daily clinical operations. Furthermore, nucleic acid stabilizers can affect downstream analyses. Described herein is the extraction of extracellular nucleic acids that can be stored at ambient temperatures until needed for downstream applications, such as PCR, without the need for additional stabilization chemicals.

The nucleic acids of the present invention can be stored at room temperature for longer than 1 week, 2 weeks, 5 weeks, 10 weeks, or 25 weeks or more.

The methodology for preparing nucleic acids in a form that is suitable for detection following collection of the cell-free salivary sample is well known in the art. Such methods can include, but are not limited to, PCR, reverse transcriptase-PCR (RT-PCR), real-time PCR, reverse transcription quantitative real-time PCR (RT-qPCR), ligase chain reaction, strand displacement amplification (SDA), self-sustained sequence replication (3SR), or in situ PCR. Any suitable qualitative or quantitative methods known in the art for detecting specific nucleic acid (e.g., RNA or DNA) can be used. Nucleic acid can be detected by, for example, by reverse transcriptase-PCR, or in Northern blots containing poly A mRNA, and other methods well known in the art.

Applicable PCR amplification techniques are described in, e.g., Ausubel et al. and Innis et al., supra. General nucleic acid hybridization methods are described in Anderson, "Nucleic Acid Hybridization," BIOS Scientific Publishers, 1999. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al., PCR Protocols, A Guide to Methods and Applications, Academic Press, Inc. N.Y. (1990).

Real time, quantitative reverse transcriptase PCR (RT-PCR), or reverse transcription quantitative real-time PCR (RT-qPCR) can be used to determine the presence of mutations. RNA extraction can be performed by any method know to those of skill in the art, e.g., methods involving proteinase K tissue digestion and alcohol-based nucleic acid precipitation, treatment with DNase to digest contaminating DNA, RNA purification using silica-gel-membrane technology, methods utilizing commercially available kits such as Trizol and RNeasy, or any combination thereof. Real time RT-PCR can be performed by any method known to those of skill in the art, e.g., Taqman real time PCR using Applied Biosystem assays.

Nucleic acid primers, or probes can be generated using the polynucleotide sequences disclosed herein. The probes are preferably at least about 12, 15, 16, 18, 20, 22, 24, or 25 nt fragments of a contiguous sequence of nucleic acid or polypeptide. The probes can be produced by, for example, chemical synthesis, PCR amplification, generation from longer polynucleotides using restriction enzymes, or other methods well known in the art.

Nucleic acid probes can be used as diagnostics wherein a biological sample to be analyzed, such as saliva, can be treated, if desired, to extract the nucleic acids contained therein. The resulting nucleic acid from the sample can be subjected to gel electrophoresis or other size separation techniques; alternatively, the nucleic acid sample can be dot blotted without size separation. The nucleic acids extracted from the sample are then treated with the labeled probe under hybridization conditions of suitable stringencies. The probes can be made completely complementary to the target nucleic acid or portion thereof (e.g., to all or a portion of a sequence encoding a target). Therefore, usually high stringency conditions are desirable in order to prevent or at least minimize false positives. However, conditions of high stringency should only be used if the probes are complementary to regions of the target which lack heterogeneity. The stringency of hybridization is determined by a number of factors during hybridization and during the washing procedure, including temperature, ionic strength, length of time, and concentration of formamide (Sambrook et al. (1989), "Molecular Cloning; A Laboratory Manual," Second Edition (Cold Spring Harbor Press, Cold Spring Harbor, N.Y.)).

Nucleic acid probes, or alternatively nucleic acid from the samples, can be provided in solution for such assays, or can be affixed to a support (e.g., solid or semi-solid support). Examples of supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride, diazotized paper, nylon membranes, activated beads, and Protein A beads.

Non-PCR-based, sequence specific DNA amplification techniques can also be used with the invention to detect nucleic acids. An example of such techniques include, but is not necessarily limited to, the Invader assay (see, e.g., Kwiatkowski et al. Mol Diagn. 1999, 4:353-64. See also U.S. Pat. No. 5,846,717).

Nucleic acids can be detectably labeled. Exemplary detectable labels include, but are not limited to, radiolabels, fluorochromes, (e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein, 6-carboxy-X-rhodamine (ROX), 6-carboxy-2',4',T,4,7-hexachlorofluorescein (HEX), 5-carboxyfluorescein (5-FAM) or N,N,N',N'-tetramethyl-6-carboxyrho-damine (TAMRA)), radioactive labels, (e.g. $^{32}P$, $^{35}S$, and $^{3}H$), and the like. The detectable label can involve two stage systems (e.g., biotin-avidin, hapten-anti-hapten antibody, and the like).

Analysis of nucleic acid mutations derived from saliva samples can be performed using techniques known in the art including, without limitation, electrophoretic analysis or sequence analysis. Non-limiting examples of electrophoretic analysis include slab gel electrophoresis such as agarose or polyacrylamide gel electrophoresis, capillary electrophoresis, and denaturing gradient gel electrophoresis (DGGE).

Other methods of nucleic acid analysis include, but is limited to, restriction analyses such as restriction-fragment-length-polymorphism detection based on allele-specific restriction-endonuclease cleavage (Kan and Dozy, Lancet ii:910-12 (1978)), hybridization with allele-specific oligonucleotide probes (Wallace et al., Nucl. Acids Res. 6:3543-3557 (1978)), including immobilized oligonucleotides (Saiki et al., PNAS 86:6230-6234 (1989)), oligonucleotide arrays (Maskos and Southern, Nucl. Acids Res. 21:2269-2270 (1993)), oligonucleotide-ligation assay (OLA) (Landegren et al., Science 241:1077 (1988)), allele-specific ligation chain reaction (LCR) (Barrany, PNAS 88:189-193 (1991)), gap-LCR (Abavaya et al. Nuc.l Acids Res. 23:675-682 (1995)), single-strand-conformation-polymorphism detection (Orita et al., Genomics 5:874-879 (1983)), RNAase cleavage at mis-matched base-pairs (Myers et al., Science 230:1242 (1985)), cleavage of heteroduplex DNA, methods based on allele specific primer extension, genetic bit analysis (GBA) (Nikiforov et al., Nucl. Acids Res. 22:4167-4175 (1994)), in situ hybridization, Southern blot, Northern blot analysis, denaturing high performance liquid chromatography (DHPLC) (Kim et al., Genetic Testing 12:295-298 (2008)). Non-limiting examples of sequence analysis include Maxam-Gilbert sequencing, Sanger sequencing, capillary array DNA sequencing, thermal cycle sequencing (Sears et al., Biotechniques, 13:626-633 (1992)), solid-phase sequencing (Zimmerman et al., Methods Mol. Cell Biol., 3:39-42 (1992)), sequencing with mass spectrometry such as matrix-assisted laser desorption/ionization time-of-flight mass spectrometry (MALDI-TOF/MS; Fu et al., Nat. Biotechnol., 16:381-384 (1998)), and sequencing by hybridization (Chee et al., Science, 274:610-614 (1996); Drmanac et al., Science, 260:1649-1652 (1993); Drmanac et al., Nat. Biotechnol., 16:54-58 (1998)), NGS (next-generation sequencing) (Chen et al., Genome Res. 18:1143-1149 (2008); Srivatsan et al. PloS Genet. 4:e1000139 (2008)), Polony sequencing (Porreca et al., Curr. Protoc. Mol. Biol. Chp. 7; Unit7.8 (2006), ion semiconductor sequencing (Elliott et al., J. Biomol Tech. 1:24-30 (2010), DNA nanoball sequencing (Kaji et al., Chem Soc Rev 39:948-56 (2010), single molecule real-time sequencing (Flusberg et al., Nat. Methods 6:461-5 (2010), or nanopore DNA sequencing (Wanunu, Phys Life Rev 9:125-58 (2012).

Probes (or sample nucleic acid) can be provided on an array for detection following saliva extraction. Arrays can be created by, for example, spotting polynucleotide probes onto a substrate (e.g., glass, nitrocellulose, and the like) in a two-dimensional matrix or array. The probes can be bound to the substrate by either covalent bonds or by non-specific interactions, such as hydrophobic interactions. Samples of polynucleotides can be detectably labeled (e.g., using radioactive or fluorescent labels) and then hybridized to the probes. Double stranded polynucleotides, comprising the labeled sample polynucleotides bound to probe polynucleotides, can be detected once the unbound portion of the sample is washed away. Techniques for constructing arrays and methods of using these arrays are described in EP 799 897; WO 97/29212; WO 97/27317; EP 785 280; WO 97/02357; U.S. Pat. No. 5,593,839; U.S. Pat. No. 5,578,832; EP 728 520; U.S. Pat. No. 5,599,695; EP 721 016; U.S. Pat. No. 5,556,752; WO 95/22058; and U.S. Pat. No. 5,631,734. Arrays are particularly useful where, for example a single sample is to be analyzed for the presence of two or more nucleic acid target regions, as the probes for each of the target regions, as well as controls (both positive and negative) can be provided on a single array. Arrays thus facilitate rapid and convenience analysis.

Protein Analysis

Embodiments described herein include a streamlined, ambient-temperature processing, stabilization, and storage of proteins derived from saliva. Direct saliva proteomic analyses using cell-free saliva supernatant instead of isolated proteins, which include the processing, stabilization, and storage of saliva samples, as described herein, can be performed at ambient temperature.

Profiling saliva proteins over the course of disease progression can reveal potential biomarkers indicative of different stages of disease, which can be useful in early detection of disease. Protein stabilization requiring extremely low temperatures or protein stabilization chemicals can be impractical for field applications or daily clinical operations. Furthermore, protein stabilizers can affect downstream analyses. In some embodiments, protein stabilizers can be used. In other embodiments, protein stabilizers are not used. In other embodiments, ethanol can be used to stabilize the salivary proteins of the present invention.

Described herein is further the addition of alcohol to increase the stability of cell-free saliva samples at ambient temperature. Without being bound by theory, alcohol could replace ordered water molecules around exposed hydrophobic groups, which surround the non-polar side chins of the proteins and thus increase the stability of salivary proteins. Alcohol can include, but it not limited to, ethanol. Alcohol can be added, for example, at concentrations of 5%, 10%, 20%, 30%, 40%, 50%, 60%, 70%, 80%, 90%, or 95% alcohol. Alcohol can be added, for example, at concentrations of 25-35%, 20-40%, 15-45%, 10-50%, 5-50%.

The nucleic acids of the present invention can be stored at room temperature for longer than 1 week, 2 weeks, 5 weeks, 10 weeks, or 25 weeks or more.

The methodology for preparing protein in a form that is suitable for detection following collection of the cell-free salivary sample is well known in the art. Extracellular protein can be purified to substantial purity by standard techniques, including selective precipitation with such substances as ammonium sulfate; column chromatography, immunopurification methods, and others (see, e.g., Scopes, Protein Purification: Principles and Practice (1982); U.S. Pat. No. 4,673,641; Ausubel et al, supra; and Sambrook et al., supra).

The molecular weight of the protein can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed.

The protein can also be separated from other proteins on the basis of its size, net surface charge, hydrophobicity, and affinity for ligands or substrates using column chromatography. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Antibody reagents can be used in assays to detect proteins in saliva samples using any of a number of immunoassays known to those skilled in the art Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used. (See, e.g., Self et al., Curr. Opin. Biotechnol 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (META); immunohistochemical assay, capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence. (See, e.g., Schmalzing et al., Electrophoresis, 25 18:2184-93 (1997); Bao, J Chromatogr. B. Biomed. Sci., 699:463-80 (1997)). Liposome immunoassays, such as flow-injection liposome immunoassays and liposome immunosensors, are also suitable for use in the present invention. (See, e.g., Rongen et al., J. Immunol. Methods, 204:105-133 (1997)). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, Calif.; Kit #449430) and can be performed using a Behring Nephelometer Analyzer (Fink et al., J Clin. Chem. Clin. Biochem., 27:261-276 (1989)).

Specific immunological binding of an antibody can be detected directly or indirectly. A detectable moiety can be used (direct or indirect detection). A variety of detectable moieties are well known to those skilled in the art, and can be any material detectable by spectroscopic, photochemical, biochemical, immunochemical, electrical, optical or chemical means. Detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, metals, and the like. Direct labels include fluorescent or luminescent tags, metals, dyes, radionucleodies, and the like, attached to the antibody. An antibody labeled with iodine-125 (125I) can be used. A chemiluminescence assay using a chemiluminescent antibody specific for nucleic acids or proteins is suitable for sensitive, non-radioactive detection of nucleic acids or protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethyl-benzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-3-D-galactopyranoside (ONPG), which yields a soluble product detectable at 410 nm. An urease detection system can be used with a substrate such as urebromocresol purple (Sigma Immunochemicals; St. Louis, Mo.). Other proteins capable of specifically binding immunoglobulin constant regions, such as protein A or protein G can also be used as a label agent. These proteins exhibit a strong non-immunogenic reactivity with immunoglobulin constant regions from a variety of species (see, e.g., Kronval et al., J. Immunol. 111:1401-1406 (1973); Akerstrom et al., J. Immunol. 135: 2589-2542 (1985).

Western blot (immunoblot) analysis can be used to detect and quantify the presence of an antigen in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the antigen. The anti-antigen antibodies specifically bind to the antigen on the solid support. These antibodies can be directly labeled or alternatively can be subsequently detected using labeled antibodies (e.g., labeled sheep anti-mouse antibodies) that specifically bind to the anti-antigen antibodies.

An ELISA method can be used as follows: (1) bind an antibody or antigen to a substrate; (2) contact the bound receptor with a fluid or tissue sample containing the virus, a viral antigen, or antibodies to the virus; (3) contact the above with an antibody bound to a detectable moiety (e.g., horseradish peroxidase enzyme or alkaline phosphatase enzyme); (4) contact the above with the substrate for the enzyme; (5) contact the above with a color reagent; (6) observe color change. The above method can be readily modified to detect presence of an antibody in the sample or a specific protein as well as a virus.

An antigen and/or a subject's antibodies to the virus can be detected utilizing a capture assay. Briefly, to detect antibodies in a sample, antibodies to an immunoglobulin, e.g., anti-IgG (or IgM) are bound to a solid phase substrate and used to capture the patient's immunoglobulin from serum. The antigen, or reactive fragments of the antigen, are then contacted with the solid phase followed by addition of a labeled antibody. The amount of specific antibody can then be quantitated by the amount of labeled antibody binding. A micro-agglutination test can also be used to detect the presence of an antigen in test samples. Briefly, latex beads are coated with an antibody and mixed with a test sample, such that the antigen in the tissue or body fluids that is specifically reactive with the antibody crosslink with the receptor, causing agglutination. The agglutinated antibody-virus complexes within a precipitate, visible with the naked eye or by spectrophotometer.

Competitive assays can also be adapted to provide for an indirect measurement of the amount of an antigen present in the sample. Briefly, serum or other body fluids from the subject is reacted with an antibody bound to a substrate (e.g. an ELISA 96-well plate). Excess serum is thoroughly washed away. A labeled (enzyme-linked, fluorescent, radioactive, etc.) monoclonal antibody is then reacted with the previously reacted antibody complex. The amount of inhibition of monoclonal antibody binding is measured relative to a control. Monoclonal antibodies (MABs) can also be used for detection directly in samples by IFA for MABs specifically reactive for the antibody-antigen complex.

A hapten inhibition assay is another competitive assay. In this assay the known antigen can be immobilized on a solid substrate. A known amount of anti-antigen antibody is added to the sample, and the sample is then contacted with the immobilized antigen. The amount of antibody bound to the known immobilized antigen is inversely proportional to the amount of antigen present in the sample. The amount of immobilized antibody can be detected by detecting either the immobilized fraction of antibody or the fraction of the antibody that remains in solution. Detection can be direct where the antibody is labeled or indirect by the subsequent addition of a labeled moiety that specifically binds to the antibody as described above.

Immunoassays in the competitive binding format can also be used for crossreactivity determinations. For example, an antigen can be immobilized to a solid support. Proteins can be added to the assay that competes for binding of the antisera to the immobilized antigen. The ability of the added proteins to compete for binding of the antisera to the immobilized protein is compared to the ability of the antigen to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs. The immunoabsorbed and pooled antisera can then be used in a competitive binding immunoassay as described above to compare a second protein, thought to be perhaps an allele or polymorphic variant of an antigen, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the antigen that is required to inhibit 50% of binding, then the second protein is said to specifically bind to the polyclonal antibodies generated to antigen.

A signal from a direct or indirect label can be analyzed, for example, using a spectrophotometer to detect color from a chromogenic substrate; a radiation counter to detect radiation such as a gamma counter for detection of 125I; or a fluorometer to detect fluorescence in the presence of light of a certain wavelength. Where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by the use of electronic detectors such as charge coupled devices (CCDs) or photomultipliers and the like. Similarly, enzymatic labels can be detected by providing the appropriate substrates for the enzyme and detecting the resulting reaction product. Colorimetric or chemiluminescent labels can be detected simply by observing the color associated with the label. Thus, in various dipstick assays, conjugated gold often appears pink, while various conjugated beads appear the color of the bead. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Saliva Collection Apparatus and Kit

Embodiments of the invention described herein relate to the analysis of extracellular nucleic acids and proteins derived from a cell-free fluid phase portion of saliva. Saliva Collection, Processing, Stabilization, and Storage (SCPSS) is designed as an all-in-one kit to collect, process, stabilize, and store saliva samples for research and clinical applications such as molecular diagnostics based on protein, RNA, and DNA.

The presence of nucleic acids and proteins in the cell-free fluid phase portion of saliva was confirmed by the procedures described in the Examples. The quality of the detected nucleic acids and proteins meet the demand for techniques such as PCR, qPCR, microarray assays, ELISA, Western blot, etc.

To obtain filtered samples, subjects can be given an absorbent pad to place under their tongue for a period of time long enough to absorb saliva. Any type of absorbent pad that absorbs saliva can be used, and SCPSS will work with any animal that produces saliva. Suitable absorbent materials can include, but are not limited to, nitrocellulose, cellulose acetate, polyethersulfur fabric, cellulose fiber such as paper strips or cotton, nylon, gel foam, fiber glass, polycarbonate, polyproplene, acetate, rayon, polyester absorbent pad, or other synthetic materials capable of collecting saliva. Any other method known in the art can be used to collect saliva. For example, the spitting method can also be used as a means of collecting a sample of saliva. An alternative method of obtaining saliva samples is a method whereby saliva is sucked out of the oral cavity by means of an aspirator. Saliva that has collected in the oral cavity can also be simply dripped out into a sample vessel.

Figure 7:
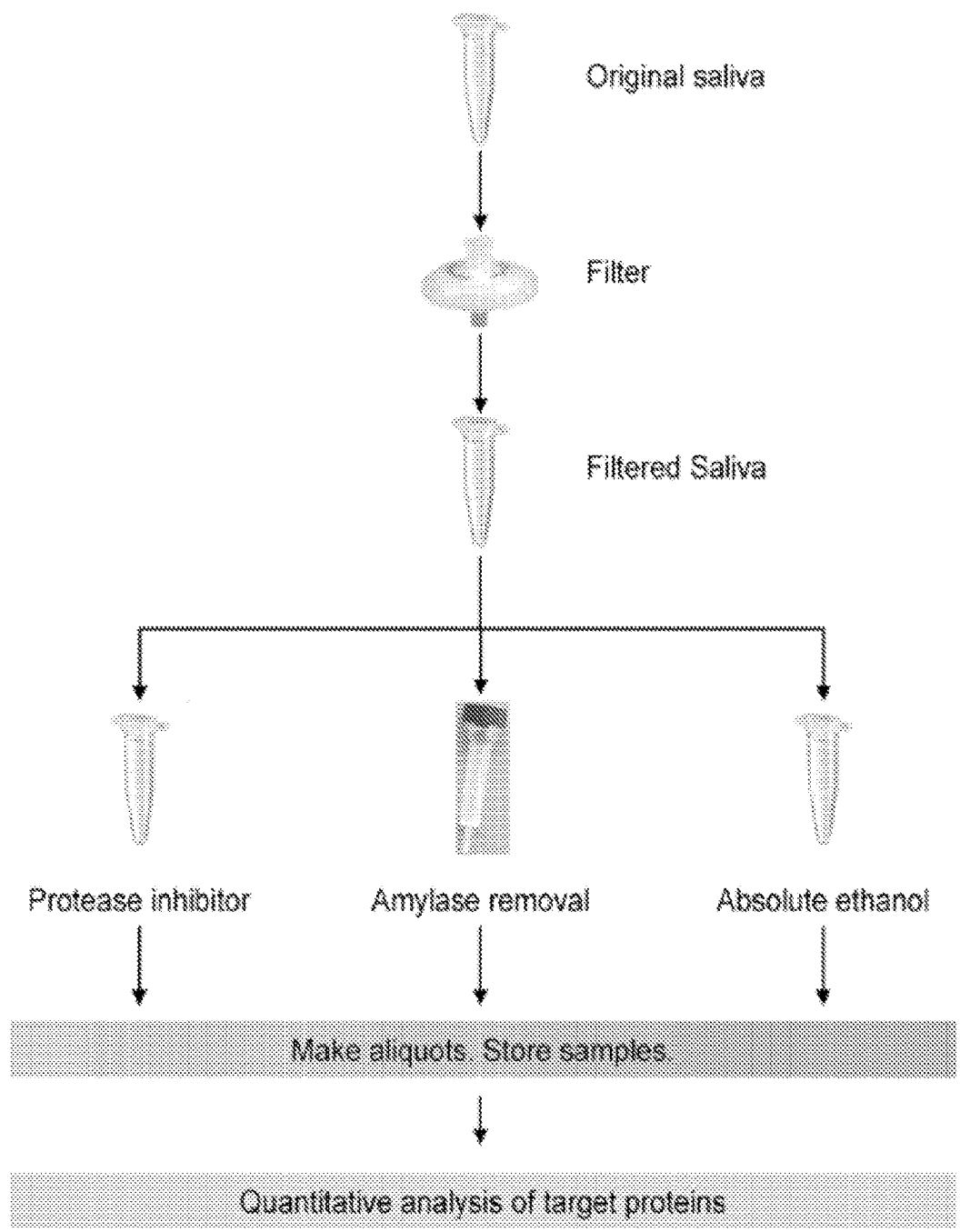
FIG. 7 illustrates a schematic diagram of the saliva sample collection and experimental design of Example 2.
Figure 13:
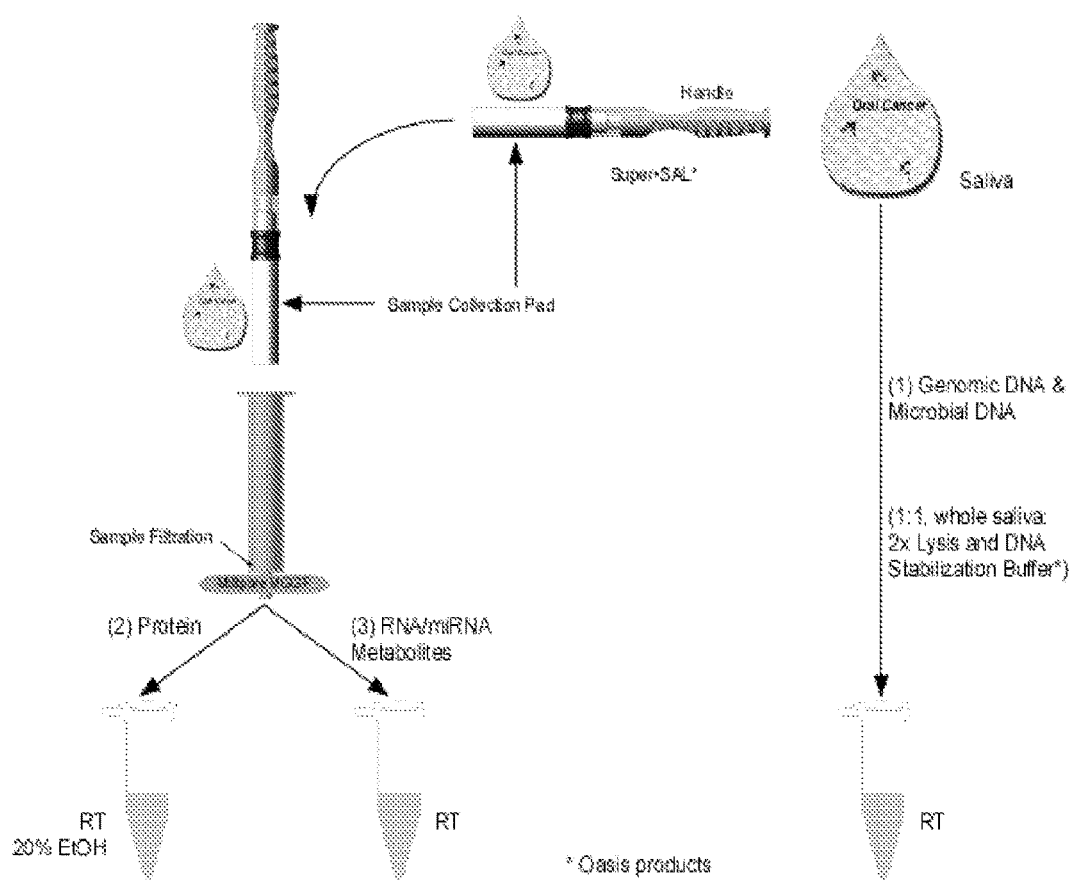
FIG. 13 illustrates depicts a scheme of saliva collection, processing, stabilization and storage (SCPSS) as described in Example 3. Provided are a syringe, absorbent pad, filter, tubes and stabilizers. The collection scheme of various biomarkers is shown.

In an embodiment, the absorbent pad can be individually placed into a syringe having a filter attached to the end of the syringe. The filter can be any type of filter described herein capable of separating saliva into a cell-free and fluid phase, for example, a 5.0 µm hydrophilic PVDF filter (Millex-SV, Millipore). The syringe plunger can then be used to push the saliva out of the pad and through the filter into a collection tube (FIG. 7). The tubes can be pre-loaded with specific stabilizer for protein, RNA, and DNA. The tubes can also be pre-loaded with an alcohol solution. The collection apparatus can be any type of commercial collection pad. For example, the SUPER●SAL or VERSI●SAL collection devices (Oasis Diagnostics, Vancouver, Wash.) can be used to collect saliva samples and further configured to be used with a sample filtration apparatus. In other embodiments, the saliva collection device can separate samples into two or more aliquots following filtration. An exemplary device for dual separation is the ULTRA●SAL-2 saliva collection device (Oasis Diagnostics, Vancouver, Wash.) (FIG. 13).

An embodiment describes the apparatus described herein in a method of for collecting saliva. The method can include inserting the sample collection pad into the oral cavity for sufficient time to moisten the sample collection pad, inserting the collection pad into the receiving tube, applying sufficient force to cause the materials collected in the collection pad to pass through the filter thereby forming a filtered sample, and collecting the filtered sample into one or more receiving devices.

It can be appreciated that classes of compounds in addition to nucleic acid and protein can be analyzed, e.g., virus, prions, bacteria (e.g., *Mycobacterium tuberculosis*), carbohydrates such as sugars, lipids, fatty acids, hormones, cholesterol, metabolites, and small molecule drug compounds.

It can further be appreciated that the apparatus can be used to diagnose a disease in a subject. The disease can include, but is not limited to, lung cancer, breast cancer stomach cancer, liver cirrhosis, a failing kidney, ulcer cancer, ovarian cancer, uterus cancer, cervical cancer, oral cancer, esophageal cancer, thyroid cancer, larynx cancer, leukemia, colon cancer, bladder cancer, prostate cancer, bronchus cancer, pancreas cancer, caries risk, periodontitis, salivary gland disease, head cancer, neck cancer, skin cancer, diabetes, smoking status, and infectious diseases such as hepatitis, HIV, and HCV. It can further be appreciated that the apparatus can be used to monitor pH levels in a subject. It can further be appreciated that the apparatus can be used to test for use of a drug including, but not limited to, prescription and controlled drugs, alcohol, methamphetamine, cocaine, caffeine, morphine, codeine, amphetamine, ephedrine, narcotine, DMT, and MDMA.

EXAMPLES

The methods system herein described are further illustrated in the following examples, which are provided by way of illustration and are not intended to be limiting.

Example 1: Direct Saliva Transcriptome Analysis (DSTA)

Standard operating procedures for salivary transcriptomic analysis require low temperatures and lengthy mRNA isolation processes. This example describes a streamlined, ambient-temperature processing, stabilization, and storage protocol for clinical analysis of salivary RNA.

Materials and Methods
DSTA Protocol

Direct Saliva transcriptome analysis (DSTA) procedures, including processing, stabilization, and storage of saliva samples, were performed at ambient temperatures and used saliva supernatant (SS) instead of isolated mRNA for saliva transcriptomic detection. SS was prepared by centrifuging collected unstimulated whole saliva at 2600 g for 15 min at 4° C., followed by aspiration from the pellet. The harvested cell-free SS was then sealed and stored in a cool, dry environment at ambient temperature without stabilizing reagent until use. The salivary mRNA was directly detected by a reverse transcription quantitative real-time PCR (RT-qPCR) assay with the stored SS used as the template.

Saliva Sample Collection and Processing

Saliva samples were collected, according to protocols approved by an institutional review board, from 5 healthy individuals (mean age 34 years) who gave informed consent. None of the individuals had a history of malignancy, immunodeficiency, autoimmune disorder, hepatitis, or HIV infection (Table 1).

TABLE 1

Information of samples used for evaluation of DSTA performance and salivary mRNA stability

| Sample ID | Ethnicity | Age | Gender | Smoking | Diagnosis |
|---|---|---|---|---|---|
| SalivaSup-1 | Asian | 34 | M | NO | Normal |
| SalivaSup-2 | Asian | 32 | M | NO | Normal |
| SalivaSup-3 | Caucasian | 33 | M | NO | Normal |
| SalivaSup-4 | Asian | 33 | F | NO | Normal |
| SalivaSup-5 | Asian | 38 | M | NO | Normal |

Abbreviations: M: Male; F: Female.

Unstimulated whole saliva samples were collected between 9 and 10 AM as described previously (NavazeshM, *Ann. NY Acad. Sci* 694: 72-7 (1994)), and processed with centrifugation to obtain cell-free SS (Li et al. *J. Dent. Res.* 183:199-203 (2004)). The absence of cells in the harvested SS was confirmed by microscopy. The collected SS of each study participant was then split into 3 aliquots (300 µL each) as diagrammed in FIG. 1. Aliquot #1 was directly transferred into a 1.5-mL microcentrifuge tube and stored. Aliquots #2 and #3 were immediately processed by DNase treatment and salivary mRNA isolation, respectively. The DNase-treated SS (product from aliquot #2) was employed as a contrast group to reflect DNA interference in the raw SS (product from aliquot #1). Isolated mRNA (product from aliquot #3) was applied to standard procedures of saliva RNA detection, and was employed as a positive control to evaluate the DSTA method performance. All the SS samples (products from aliquots #1 and #2) were stored at room temperature (25° C.) without stabilizing reagent, and the isolated mRNAs were frozen at −80° C. until use. At day 0 (i.e., the day that all samples were collected), and after 1, 2, and 10 weeks of storage, the RT-qPCR assay was used in all samples to detect mRNA expression levels of 3 saliva internal reference genes (SIRGs): glyceraldehyde-3-phosphate dehydrogenase (GAPDH), 9 actin, beta (ACTB), and ribosomal protein S9 (RPS9). The effectiveness of the DSTA method was assessed by comparing mRNA expression levels from 3 SIRGs obtained from raw SS and isolated mRNA. The stability of salivary mRNA stored at ambient temperature without stabilizing reagent was evaluated by detecting the change of each mRNA expression level in raw SS during 10 weeks of storage.

A case-control salivary biomarker study was further conducted to examine the feasibility of clinical applications of the DSTA method associated with long-term ambient temperature storage. Ninety samples were collected from 3 institutions, including 27 samples from patients with oral squamous cell carcinoma (OSCC) and 63 samples from healthy controls (see Table 2).

TABLE 2

Information of samples used for DSTA oral cancer mRNA biomarkers validation.

| Validation Sample ID | Ethnicity | Age | Gender | Smoking | Diagnosis |
|---|---|---|---|---|---|
| V-OralCAN-001 | Caucasian | 59 | M | NO | OSCC |
| V-OralCAN-002 | Caucasian | 76 | M | YES | OSCC |
| V-OralCAN-003 | Caucasian | 64 | F | YES | OSCC |
| V-OralCAN-004 | Caucasian | 61 | M | YES | OSCC |
| V-OralCAN-005 | Caucasian | 59 | M | YES | OSCC |
| V-OralCAN-006 | Caucasian | 60 | M | YES | OSCC |
| V-OralCAN-007 | Caucasian | 59 | M | NO | OSCC |
| V-OralCAN-008 | Caucasian | 65 | M | NO | OSCC |
| V-OralCAN-009 | Hispanic | 77 | M | YES | OSCC |
| V-OralCAN-010 | Caucasian | 68 | F | NO | OSCC |
| V-OralCAN-011 | Caucasian | 68 | M | NO | OSCC |
| V-OralCAN-012 | Caucasian | 59 | M | NO | OSCC |
| V-OralCAN-013 | Caucasian | 65 | F | NO | OSCC |
| V-OralCAN-014 | Caucasian | 74 | M | YES | OSCC |
| V-OralCAN-015 | Caucasian | 51 | M | YES | OSCC |
| V-OralCAN-016 | Caucasian | 78 | M | YES | OSCC |
| V-OralCAN-017 | Caucasian | 51 | M | NO | OSCC |
| V-OralCAN-018 | Caucasian | 70 | M | YES | OSCC |
| V-OralCAN-019 | Caucasian | 84 | M | YES | OSCC |
| V-OralCAN-020 | Asian | 54 | F | NO | OSCC |
| V-OralCAN-021 | Caucasian | 81 | M | NO | OSCC |
| V-OralCAN-022 | Caucasian | 63 | M | NO | OSCC |
| V-OralCAN-023 | Caucasian | 66 | M | NO | OSCC |
| V-OralCAN-024 | Caucasian | 52 | M | YES | OSCC |
| V-OralCAN-025 | Hispanic | 71 | M | NO | OSCC |
| V-OralCAN-026 | Hispanic | 49 | M | NO | OSCC |
| V-OralCAN-027 | Caucasian | 71 | M | NO | OSCC |
| V-Ctrl-001 | Caucasian | 65 | M | NO | Normal |
| V-Ctrl-002 | Caucasian | 66 | M | YES | Normal |
| V-Ctrl-003 | Caucasian | 65 | F | NO | Normal |
| V-Ctrl-004 | Caucasian | 56 | F | NO | Normal |
| V-Ctrl-005 | Caucasian | 62 | M | YES | Normal |
| V-Ctrl-006 | Caucasian | 69 | M | NO | Normal |
| V-Ctrl-007 | Caucasian | 74 | M | NO | Normal |
| V-Ctrl-008 | Caucasian | 62 | M | NO | Normal |
| V-Ctrl-009 | Caucasian | 80 | M | YES | Normal |
| V-Ctrl-010 | Caucasian | 52 | M | NO | Normal |
| V-Ctrl-011 | Caucasian | 69 | M | YES | Normal |
| V-Ctrl-012 | Caucasian | 75 | M | NO | Normal |
| V-Ctrl-013 | Hispanic | 54 | M | YES | Normal |
| V-Ctrl-014 | Caucasian | 57 | F | NO | Normal |
| V-Ctrl-015 | Caucasian | 72 | M | NO | Normal |
| V-Ctrl-016 | Asian | 37 | M | NO | Normal |
| V-Ctrl-017 | Hispanic | 64 | M | YES | Normal |
| V-Ctrl-018 | Hispanic | 45 | M | NO | Normal |
| V-Ctrl-019 | Caucasian | 56 | F | NO | Normal |
| V-Ctrl-020 | Caucasian | 59 | M | NO | Normal |
| V-Ctrl-021 | Caucasian | 60 | M | NO | Normal |
| V-Ctrl-022 | Hispanic | 63 | M | YES | Normal |
| V-Ctrl-023 | Caucasian | 57 | M | YES | Normal |
| V-Ctrl-024 | Caucasian | 72 | M | YES | Normal |
| V-Ctrl-025 | Caucasian | 62 | M | NO | Normal |
| V-Ctrl-026 | Caucasian | 66 | M | NO | Normal |
| V-Ctrl-027 | Caucasian | 72 | M | NO | Normal |
| V-Ctrl-028 | Caucasian | 56 | M | YES | Normal |
| V-Ctrl-029 | Hispanic | 62 | F | NO | Normal |
| V-Ctrl-030 | Caucasian | 57 | M | YES | Normal |
| V-Ctrl-031 | Caucasian | 45 | M | NO | Normal |
| V-Ctrl-032 | Caucasian | 54 | F | YES | Normal |
| V-Ctrl-033 | Caucasian | 52 | M | YES | Normal |
| V-Ctrl-034 | Caucasian | 62 | M | YES | Normal |
| V-Ctrl-035 | Caucasian | 55 | M | YES | Normal |
| V-Ctrl-036 | Caucasian | 70 | M | NO | Normal |
| V-Ctrl-037 | Caucasian | 67 | F | NO | Normal |
| V-Ctrl-038 | Hispanic | 35 | M | NO | Normal |
| V-Ctrl-039 | Caucasian | 81 | M | NO | Normal |
| V-Ctrl-040 | Caucasian | 59 | F | YES | Normal |
| V-Ctrl-041 | Caucasian | 61 | M | NO | Normal |
| V-Ctrl-042 | Caucasian | 63 | M | YES | Normal |
| V-Ctrl-043 | Caucasian | 71 | M | NO | Normal |
| V-Ctrl-044 | Caucasian | 62 | M | NO | Normal |
| V-Ctrl-045 | Caucasian | 54 | M | YES | Normal |
| V-Ctrl-046 | Hispanic | 64 | M | NO | Normal |
| V-Ctrl-047 | Caucasian | 64 | M | YES | Normal |
| V-Ctrl-048 | Caucasian | 59 | M | NO | Normal |
| V-Ctrl-049 | Caucasian | 58 | M | YES | Normal |
| V-Ctrl-050 | Caucasian | 66 | M | NO | Normal |
| V-Ctrl-051 | Caucasian | 77 | M | YES | Normal |
| V-Ctrl-052 | Caucasian | 70 | M | NO | Normal |
| V-Ctrl-053 | Asian | 44 | M | NO | Normal |
| V-Ctrl-054 | Caucasian | 61 | M | YES | Normal |
| V-Ctrl-055 | Caucasian | 51 | M | NO | Normal |
| V-Ctrl-056 | Caucasian | 74 | M | YES | Normal |
| V-Ctrl-057 | Caucasian | 61 | M | NO | Normal |
| V-Crtl-058 | Caucasian | 61 | M | YES | Normal |
| V-Ctrl-059 | Caucasian | 82 | M | YES | Normal |
| V-Ctrl-060 | Caucasian | 57 | M | NO | Normal |
| V-Ctrl-061 | Caucasian | 47 | M | YES | Normal |
| V-Ctrl-062 | Caucasian | 61 | M | YES | Normal |
| V-Ctrl-063 | Caucasian | 47 | M | NO | Normal |

Abbreviations: M: Male; F: Female; OSCC: Oral squamous cell carcinoma.

Ninety saliva samples were recruited from three institutions: University of California, Los Angeles (UCLA), University of Southern California (USC), and the Veterans Hospital of Greater Los Angeles (VAGLA).

All patients had a diagnosis of primary OSCC and had not undergone chemotherapy and/or radiotherapy. The controls were matched by sex, age, ethnicity, and smoking history to the OSCC group as described in Table 3.

TABLE 3

Demongraphic information for participants in the OSCC mRNA biomarker validation study.

| Demographic variable | OSCC (n = 27) | Healthy control (n = 63) |
|---|---|---|
| Age, mean (SD), y | 65.00 (9.56) | 61.29 (9.82) |
| Sex, n (%) | | |
| Male | 23 (85.2) | 55 (87.3) |
| Female | 4 (14.8) | 8 (12.7) |
| Ethnicity, n (%) | | |
| White | 23 (85.2) | 54 (85.7) |
| Hispanic | 3 (11.1) | 7 (11.1) |
| Asian | 1 (3.7) | 2 (3.2) |
| Smoking, n (%) | | |
| Yes | 12 (44.4) | 27 (42.9) |
| No | 15 (55.6) | 36 (57.1) |

The saliva collection procedures were approved by the ethics review boards and institutional review boards of all participating institutions. All participants provided written informed consent before sample collection. In this study, we used mRNAs from 7 OSCC salivary biomarker genes: human H3 histone family 3A (H3F3A), interleukin)-beta (IL1B), interleukin 8 (IL8), ornithine decarboxylase antizyme 1 (OAZ1), spermidine/spermine N1-acetyltransferase 1 (SAT1), dual specificity phosphatase1 (DUSP1), and S100 calcium binding protein P (S100P) (Li et al. *Clin. Cancer Res.* 10:8442-50 (2004)). These biomarker genes were used as the proof-of-concept markers and tested in all study participants. Quantification of the 7 transcripts in 90 samples was performed concurrently by standard and DSTA methods at day 0 and after 10 weeks of ambient temperature storage without a stabilizing reagent. The feasibility of the DSTA method for the clinical applications was evaluated by the numbers of markers that could be discriminated, and their diagnostic performances were compared to the results obtained by standard procedures.

DNase Treatment

Figure 2:
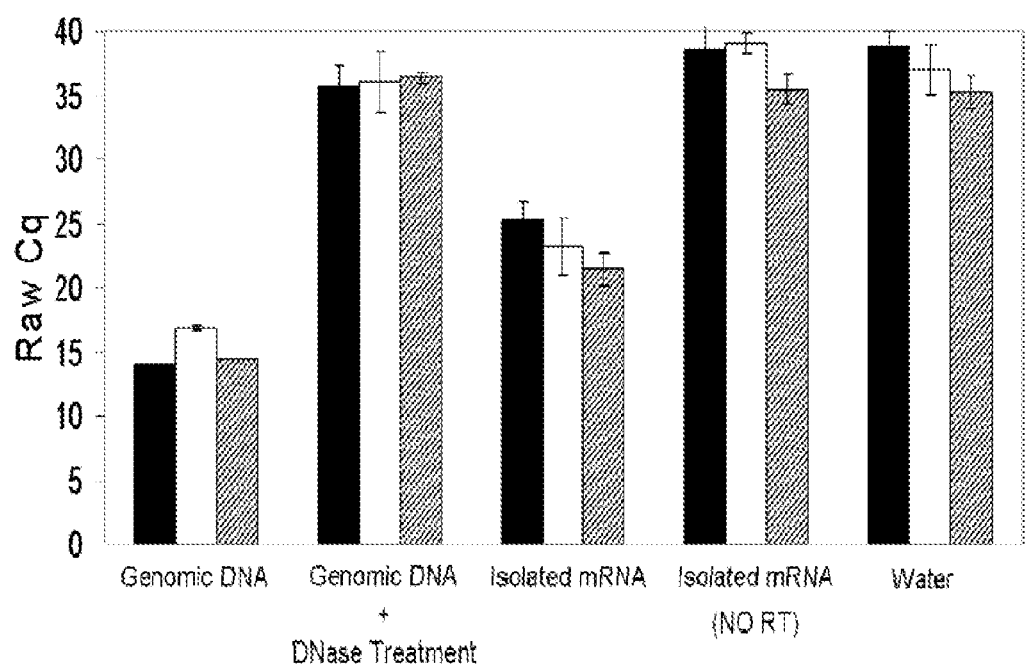
FIG. 2 illustrates the effect of DNA removal by the described DNase treatment procedures as demonstrated using human cell genomic DNA (300 µg/ml) as template. Solid bars represent GAPDH, white bars represent ACTB, and striped bars represent RPS9.

Genomic DNA was eliminated in 40 µL SS (FIG. 1, aliquot #2 of each study participant) by rigorous DNase treatment using a TURBO DNA-Free™ kit (Applied Biosystems) followed by DNase inactivation according to the manufacturer's instructions. The effect of DNA removal was demonstrated by applying human cell genomic DNA (300 µg/mL) to the above DNase treatment procedures. (FIG. 2).

Salivary mRNA Isolation

Salivary mRNA was isolated from 300 µL SS (FIG. 1, aliquot #3 of each study participant) using a King-Fisher® instrument (Thermo Electron Corporation) with a MagMAX Viral RNA Isolation Kit® (Applied Biosystems). The isolated mRNA was then treated with a TURBO DNA-free kit, followed by DNase inactivation to remove DNA contamination. The purity of the isolated mRNA was assessed by use of the A260/A280 ratio (accepted range: 1.8-2.0) with an ND-1000 spectrophotometer (Thermo Scientific). The complete removal of DNA in the isolated mRNA was demonstrated by qPCR without reverse transcription (see FIG. 2). Furthermore, the quality of isolated mRNAs was evaluated by detecting GAPDH, ACTB, and RPS9 mRNA expression levels using an RT-qPCR assay. Only those samples exhibiting PCR products for all 3 genes were used for subsequent analyses (Li et al. *Clin. Cancer Res.* 10:8442-50 (2004)).

RT-qPCR

A 2-step RT-qPCR (reverse transcription-PCR (RT-PCR) followed by qPCR operated separately) was performed for detection of salivary transcriptomes. Multiplex RT-PCR preamplification of 3 SIRG mRNAs was performed by using a SuperScript III platinum qRT-PCR System (Invitrogen) with a pool of outer primer sets (200 nmol/L for each; see Table 4), and conducted by a GeneAmp PCR-System 9700 (Applied Biosystems) with a fixed thermal cycling program (see Table 5). Each study participant provided 6 L raw SS, 7.08 µL DNase-treated SS, and 2 µL isolated mRNA as 3 different templates for RT-PCR, in which the samples were equalized by the mRNA volume. In addition to the 15 experimental RT-PCR samples (5 study participants 3 templates per study participant), a negative control with nuclease-free water as the reactive template (i.e., a blank group) was prepared. The total volume of each reaction was 30 µL adjusted by nuclease free water. The RT-PCR products were purified by ExoSAP-IT (USB) and immediately applied to qPCR or stored at −20° C. until use.

TABLE 4

Primers of 3 SIRGs and 7 OSCC salivary transcripts

| Gene Symbol | NCBI Accession No. | Primer sequences (5' to 3') | Amplicon Size (bp) |
|---|---|---|---|
| GAPDH | NM_002046 | OF: CCTCAACGACCACTTTGTCA (SEQ ID NO: 1)<br>OR: ATGTGGGCCATGAGGTCC (SEQ ID NO: 2)<br>IF: ACCACTTTGTCAAGCTCATTTCCT (SEQ ID NO: 3)<br>IR: CACCCTGTTGCTGTAGCCAAAT (SEQ ID NO: 4) | 59 |
| ACTB | NM_001101 | OF: GATCATTGCTCCTCCTGAGC (SEQ ID NO: 5)<br>OR: CGGACTCGTCATACTCCTGC (SEQ ID NO: 6)<br>IF: CTCCTGAGCGCAAGTACTCC (SEQ ID NO: 7)<br>IR: ATACTCCTGCTTGCTGATCCAC (SEQ ID NO: 8) | 92 |
| RPS9 | NM_001013 | OF: ATCTCGTCTCGACCAAGAGC (SEQ ID NO: 9)<br>OR: TTTGACCCTCCAGACCTCAC (SEQ ID NO: 10)<br>IF: CGACCAAGAGCTGAAGCTGAT (SEQ ID NO: 11)<br>IR: CCAGACCTCACGTTTGTTCC (SEQ ID NO: 12) | 58 |
| H3F3A | NM_002107 | OF: AGCGTCTGGTGCGAGAAATT (SEQ ID NO: 13)<br>OR: GCACACAGGTTGGTGTCTTCAA (SEQ ID NO: 14)<br>IF: CGCTTCCAGAGCGCAGCTAT (SEQ ID NO: 15)<br>IR: TCTTCAAAAAGGCCAACCAGAT (SEQ ID NO: 16) | 71 |
| IL1B | NM_000576 | OF: GTACCTGTCCTGCGTGTTGAAAG (SEQ ID NO: 17)<br>OR: TTCTATCTTGTTGAAGACAAATCGCTT (SEQ ID NO: 18)<br>IF: TGTTGAAAGATGATAAGCCCACTCT (SEQ ID NO: 19)<br>IR: CAAATCGCTTTTCCATCTTCTTCT (SEQ ID NO: 20) | 84 |
| IL8 | NM_000584 | OF: TTTCTGATGGAAGAGAGCTCTGTCT (SEQ ID NO: 21)<br>OR: ATCTTCACTGATTCTTGGATACCACA (SEQ ID NO: 22)<br>IF: CCAAGGAAAACTGGGTGCAG (SEQ ID NO: 23)<br>IR: CTTGGATACCACAGAGAATGAATTTTT (SEQ ID NO: 24) | 89 |
| OAZ1 | NM_004152 | OF: TGCGAGCCGACCATGTC (SEQ ID NO: 25)<br>OR: CCCCGGTCTCACAATCTCAA (SEQ ID NO: 26)<br>IF: TCTTCATTTGCTTCCACAAGAACC (SEQ ID NO: 27)<br>IR: TCAAAGCCCAAAAAGCTGAAG (SEQ ID NO: 28) | 73 |
| SAT1 | NM_002970 | OF: CGTGATGAGTGATTATAGAGGCTTTG (SEQ ID NO: 29)<br>OR: GGTTCATTCCATTCTGCTACCAA (SEQ ID NO: 30)<br>IF: TTGGCATAGGATCAGAAATTCTGAA (SEQ ID NO: 31)<br>IR: TCTGCTACCAAGAAGTGCATGCT (SEQ ID NO: 32) | 85 |
| DUSP1 | NM_004417 | OF: CCTGTGGAGGACAACCACAAG (SEQ ID NO: 33)<br>OR: GCCTGGCAGTGGACAAACA (SEQ ID NO: 34) | 75 |

TABLE 4-continued

Primers of 3 SIRGs and 7 OSCC salivary transcripts

| Gene Symbol | NCBI Accession No. | Primer sequences (5' to 3') | Amplicon Size (bp) |
|---|---|---|---|
| | | IF: CAGACATCAGCTCCTGGTTCAA (SEQ ID NO: 35) | |
| | | IR: CAAACACCCTTCCTCCAGCAT (SEQ ID NO: 36) | |
| S100P | NM_005980 | OF: GCACGCAGACCCTGACCA (SEQ ID NO: 37) | 72 |
| | | OR: CGTCCAGGTCCTTGAGCAATT (SEQ ID NO: 38) | |
| | | IF: GCTGATGGAGAAGGAGCTACCA (SEQ ID NO: 39) | |
| | | IR: TTGAGCAATTTATCCACGGCAT (SEQ ID NO: 40) | |

Abbreviations:
NCBI: National Center for Biotechnology Information;
O: outer;
I: inner;
F: forward;
R: reverse.
Amplicon size: The product size yielded by IF + IR

TABLE 5

Thermal cycling program for RT-PCR preamplification.

| Temperature (° C.) | Time | Cycle |
|---|---|---|
| 60 | 2 min | 1 |
| 50 | 30 min | |
| 95 | 2 min | |
| 95 | 15 sec | 15 |
| 50 | 30 sec | |
| 60 | 10 sec | |
| 72 | 10 sec | |
| 72 | 10 min | 1 |
| 4 | Forever | |

SYBR Green qPCR was performed to quantitatively detect the expression levels of salivary transcripts. The qPCR sample was prepared by combining 2×qPCR Mastermix (Applied Biological Materials), inner primers (900 nmol/L; see Table 4), and 2 μL cDNA template. The total volume of each reaction was 10 μL adjusted by nuclease-free water. The qPCR associated with melting-curve analysis was conducted by use of an AB-7500HT System (Applied Biosystems) with a fixed thermal-cycling program (Table 6). Each gene was tested in triplicate for all samples, including the negative control in which the cDNA template was the product of negative control in RT-PCR preamplification. All primers used in RT-qPCR were designed with intron spanning by use of PRIMER3 software and produced by Sigma after a BLAST search.

TABLE 6

Thermal cycling program for qPCR.

| Mode | Temperature (° C.) | Time | Cycle |
|---|---|---|---|
| Hot Start | 95 | 20 sec | 1 |
| qPCR | 95 | 3 sec | 40 |
| (Quick AB 7500) | 60 | 30 sec | |
| | 95 | 15 sec | |
| | 60 | 1 min | 1 |
| Disassociation | 95 | 15 sec | |
| Stage | 60 | 15 sec | |

Statistical Analysis

The expression levels of 3 SIRG mRNAs and 7 OSCC salivary transcripts detected by the streamlined and standard procedures were analyzed by raw quantification cycle (Cq) values. All qPCR experiments were performed in triplicate and presented as mean (SD) Cq. Statistical comparison by ANOVA was performed at a significance level of $P<0.05$ based on the Wilcoxon signed-rank test. In the case-control salivary biomarker study, the transcript was validated when it showed a significantly different level ($P<0.05$) between the OSCC patients and controls. In addition, the ROC curve was constructed and the value of the area under the curve (AUC) was calculated by numerical integration of the ROC curve using MedCalc software for each transcript detected. The P values between OSCC and controls combined with AUC values represent the diagnostic performance of the biomarker.

Results

Figure 3:
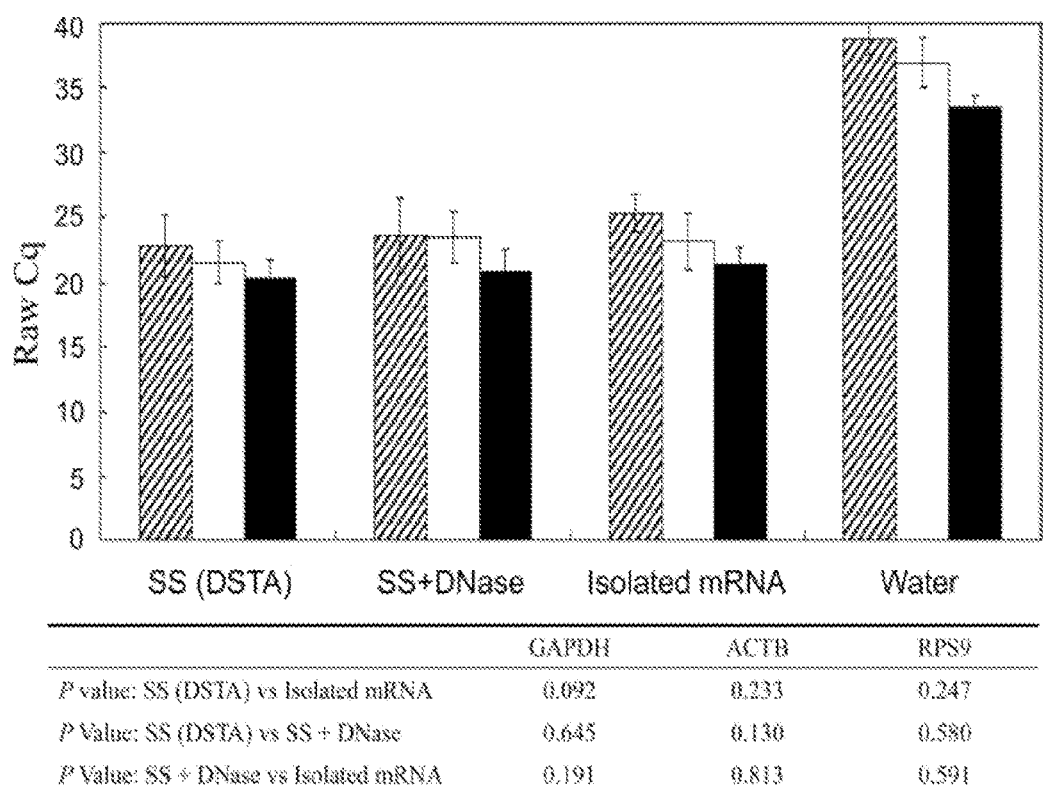
FIG. 3 illustrates expression levels of 3 SIRG mRNAs analyzed by standard procedures and the DSTA method at day 0.
Figure 5:
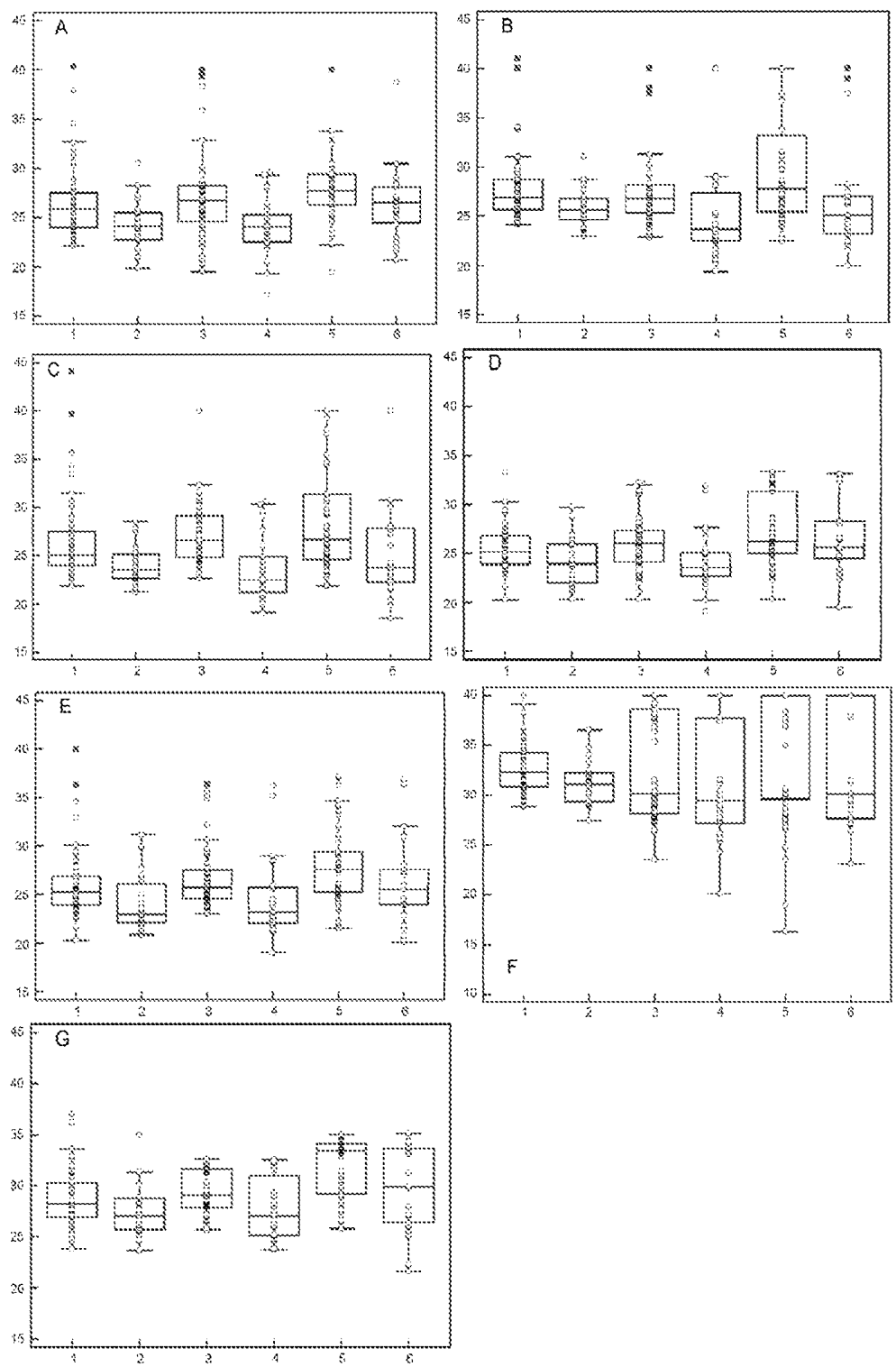
FIG. 5A-G illustrates box-and-whisker plots showing the Cq value distributions of 90 clinical samples used in the validation study of OSCC salivary transcripts. The results of each transcript were displayed individually in (A) H3F3A; (B) IL1B; (C) IL8; (D) OAZi; (E) SAT1; (F) DUSP1, and (G) S100P. Each transcript was detected in 27 OSCC and 63 normal subjects by standard and streamlined procedures at Day 0 and Week 10 (DSTA method only), which were represented by 1-6 on X axis: 1: Normal subjects assayed by standard procedures; 2: OSCC subjects assayed by standard procedures; 3: Normal subjects assayed by the SDTA method of Day 0; 4: OSCC subjects assayed by the DSTA method at Day 0; 5: Normal subjects assayed by the DSTA method at Week 10; and 6: OSCC subjects assayed by the DSTA method at Week 10. Y axis is represented by raw Cq value in each plot.

To explore whether salivary transcriptomes can be directly detected without the need for RNA isolation, cell-free SS was used as a template to detect mRNA expression levels for 3 SIRGs and compared the results to results obtained with standard procedures. The results shown in FIG. 3 are for detection performed immediately after saliva samples were collected (day 0). The Cq value in the water group is the mean of triplicate qPCR experiments, and showed 33 for all 3 genes. In addition, the water group did not show any peak in the melting-curve analysis (data not shown), no matter which SIRG primers were used, indicating there was no reagent contamination during the RT-qPCR procedures. The Cq value of each gene in the experimental setups (SS (DSTA), SS+DNase, and isolated mRNA) was the mean of results for samples from 5 healthy study participants, each of which was assayed in triplicate (total 15 data points). The Cq values obtained from the raw SS (DSTA) were 22.84 (2.36), 21.57 (1.63), and 20.35 (1.39), whereas the Cq acquired from isolated mRNAs were 25.28 (1.44), 23.16 (2.2), and 21.42 (1.33) for GAPDH, ACTB, and RPS9, respectively. The P values obtained by comparing the Cq values from SS (DSTA) and isolated mRNA for each SIRG were 0.092, 0.233, and 0.247 for GAPDH, ACTB, and RPS9, respectively. To ensure that the obtained Cq values resulted from the specific mRNA without genomic DNA interference, melting-curve analyses were conducted along with each qPCR run. A single peak with similar melting temperature was observed for the same gene in all samples (data not shown). Furthermore, when we compared the Cq values of the SIRGs in the DNase-treated SS group to the values for the SS(DSTA) group, the P values were 0.645, 0.13, and 0.58 for GAPDH, ACTB, and RPS9, respectively (FIG. 3; P value: SS (DSTA) vs SS+DNase). These results indicated that the results in the SS (DSTA) group were exclusively from the mRNA without DNA interference, and the performance of the DSTA method was comparable to the positive control. The quantitative distributions of Cq values for each transcript in healthy controls and patients with OSCC are shown in FIG. 5 and statistically described in Table 7.

TABLE 7

Statistical analyses of 7 OSCC salivary mRNA biomarkers assayed by the streamlined and standard procedures and detected at day 0 and after 10 weeks of storage.

| Gene symbol | Standard procedures (Isolated mRNA) | | | DSTA day 0 (Saliva supernatant) | | | DSTA week 10 at room temperature (Saliva supernatant) | | |
|---|---|---|---|---|---|---|---|---|---|
| | P | AUC | $\Delta Cq^b$ | P | AUC | $\Delta Cq$ | P | AUC | $\Delta Cq$ |
| H3F3A | $0.004^b$ | 0.655 | 1.77 | $<0.001^c$ | 0.718 | 2.8 | $0.012^c$ | 0.669 | 2.3 |
| IL1B | $0.002^b$ | 0.677 | 1.73 | $0.015^c$ | 0.745 | 2.8 | $0.02^c$ | 0.707 | 3.2 |
| IL8 | $0.005^b$ | 0.655 | 1.78 | $<0.001^c$ | 0.805 | 3.6 | $0.005^c$ | 0.712 | 3.6 |
| OAZ1 | $0.003^b$ | 0.688 | 1.59 | $0.014^c$ | 0.684 | 1.7 | 0.345 | 0.560 | 0.8 |
| SAT1 | $0.044^b$ | 0.667 | 1.40 | $0.028^c$ | 0.728 | 2.0 | 0.085 | 0.650 | 1.7 |
| DUSP1 | $0.008^b$ | 0.644 | 1.56 | 0.214 | 0.585 | 1.7 | $0.048^c$ | 0.636 | 2.8 |
| S100P | 0.092 | 0.611 | 0.93 | $0.008^c$ | 0.693 | 1.8 | $0.025^c$ | 0.662 | 2.0 |

[a]RT-qPCR was performed to validate the 7 previously identified OSCC biomarkers in an independent clinical saliva sample, including 27 OSCC patients and 63 healthy controls.
[b]ΔCq: the mean Cq value of 63 healthy controls − the mean Cq value of 27 OSCC patients.
[c]The marker is validated if P < 0.05 based on Wilcoxon signed-rank test.

standard procedures for salivary mRNA detection. It should be noted that both the outer and inner primers of SIRGs were designed by intron spanning, which provided additional specificity to the mRNA assays.

To evaluate the stability of saliva mRNA at room temperature without stabilizing reagent and/or nuclease inhibitor, saliva samples were stored at 25° C. (laboratory ambient temperature), and the 3 SIRG mRNA expression levels were assayed by using RT-qPCR at day 0 and after 1, 2, and 10 weeks of storage. As shown in FIG. 4 for the 3 SIRGs evaluated, the mean Cq values detected by SS (DSTA) increased slightly after 10 weeks of preservation and showed no significant difference throughout the time course (P>0.05; FIG. 4; P values: SS(DSTA)-Week X vs SS (DSTA)-Day 0 at ×10). In addition, the Cq values obtained by using SS were all similar to those detected by isolated mRNA (P>0.05) at each time point (FIG. 4; P value: SS(DSTA) vs isolated mRNA at day 0 and weeks 1, 2, and 10). DNase-treated SS samples were used to assess DNA contamination for the duration of ambient temperature storage. As shown in FIG. 4, the mean Cq values were all similar to the results detected by raw SS (P>0.05) at each time point, indicating no DNA interference was present in the DSTA procedure (FIG. 4; P values: SS (DSTA) vs SS+DNase at day 0 and weeks 1, 2, and 10). These results demonstrated that mRNA in SS can be stable at ambient temperature in the absence of stabilizing reagent for up to 10 weeks without significant degradation, and analyzed by the DSTA method.

Figure 6:
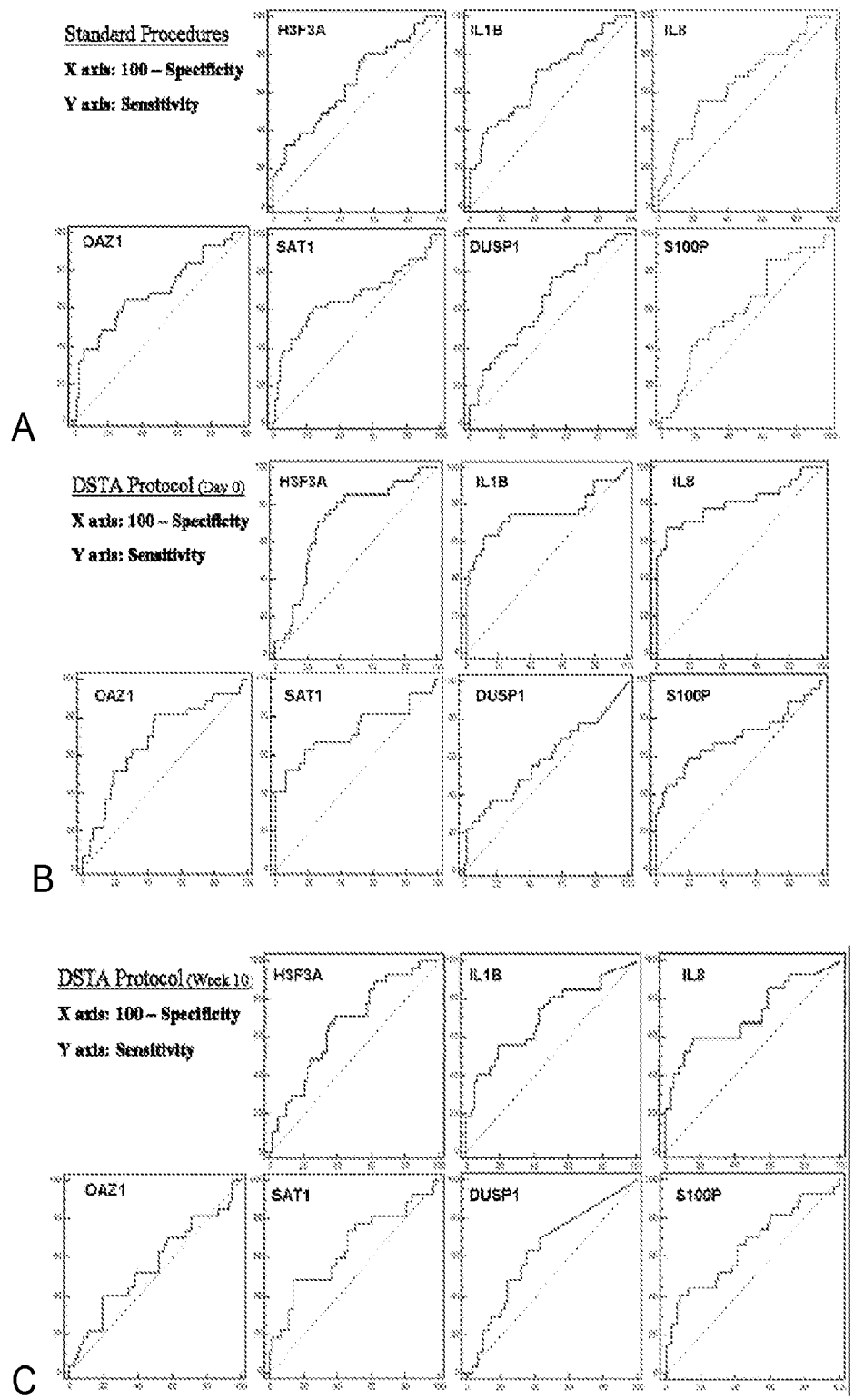
FIG. 6A-C illustrates (A) ROC curves for 7 OSCC salivary transcripts that was each detected by standard procedures, (B) ROC curves for 7 OSCC salivary transcripts that each was detected by the DSTA at day 0, and (C) ROC curves for 7 OSCC salivary transcripts that each was detected by the DSTA at week 10.

With the observed performance of the DSTA method, the feasibility of DSTA was evaluated in a clinical study. Ninety saliva samples (27 from OSCC patients and 63 from matched controls) were assayed for 7 previously identified OSCC salivary RNA markers: SAT1, OAZ1, H3F3A, IL1B, IL8, DUSP1, and S100P (Li et al. *Clin. Cancer Res.* 10:8442-50 (2004)). To examine the effect of long-term ambient temperature storage on marker discrimination, 7 salivary transcripts by the were assayed by the DSTA method at day 0 (i.e., immediately after sample collection) and after 10 weeks of room temperature storage without stabilizing reagent. Identification of the 7 salivary transcripts by using standard procedures was performed in parallel as All 7 salivary oral cancer RNA markers exhibited upregulation in the OSCC cohort assayed by both DSTA and standard procedures. By standard procedures, 6 of the 7 gene transcripts, H3F3A, IL1B, IL8, OAZ1, SAT1, and DUSP1, showed significantly different expression levels between normal and OSCC samples (P<0.05). With the DSTA method, 6 (H3F3A, IL1B, IL8, OAZ1, SAT1, and S100P) and 5 (H3F3A, IL1B, IL8, DUSP1, and S100P) of the 7 oral cancer markers were validated (P<0.05) at day 0 and week 10, respectively. Five (H3F3A, IL1B, IL8, OAZ1, and SAT1) and 4 (H3F3A, IL1B, IL8, and DUSP1) of the salivary oral cancer markers were validated by both standard procedures and the DSTA method at day 0 and week 10, respectively. Of note, 4 markers (H3F3A, IL1B, IL8, and SAT1) at day 0 and 3 markers (H3F3A, IL1B, and IL8) at week 10 exhibited higher ROC-plot AUC values when assayed by use of the DSTA protocol (see Table 7 FIG. 6). These results indicate that the DSTA method is comparable to standard procedures in discrimination of oral cancer salivary mRNA biomarkers.

Discussion

Saliva RNA detection is an emerging field in molecular diagnostics (Martin et al. *Cancer Res.* 70:5203-6 (2010)). This study aimed to develop a robust, easy-to-use, ambient-temperature compatible, and cost-effective protocol to further advance the use of saliva transcriptomes for translational and clinical applications.

This study shows that 3 SIRG mRNA expression levels remained stable in ambient temperature-stored saliva supernatant for up to 10 weeks. This outcome is consistent with results showing that salivary RNAs are protected by specific mechanisms against nucleases in saliva. Without being bound by theory, this protective phenomenon may because salivary RNAs are associated with macromolecules such as mucines, AU (adenine and uridine)-rich element binding protein, salivary chaperone Hsp70, and apoptotic bodies. Exosomes may also play an important role in protecting salivary transcriptomes, which are vesicles for intercellular mRNA transfer that have been found in saliva. Exosomes may provide a shelter to confer salivary mRNA stability in the presence of extracellular RNases. Furthermore, analyses of the RNA profiles in exosomes showed that ribosomal RNA was absent and most of the RNA molecules were <200 nucleotides in length (Skog et al, *Nat. Cell Biol.* 10:1470 (2008)), which is in alignment with the mean size of salivary mRNA.

A clinical validation study of 7 oral cancer salivary mRNA biomarkers was performed previously (Li et al. *Clin. Cancer Res.* 10:8442-50 (2004)) to evaluate the clinical performance of the DSTA method. The number of validated salivary RNA markers was benchmarked (i.e., the transcript showing significant upregulation in OSCC patients; P<0.05) and their diagnostic performances, and compared these results with the results assayed by the DSTA method. The quality of the products obtained by standard and DSTA procedures was evaluated by running melting curves along with all qPCR assays. All samples exhibited a single peak with a similar melting temperature for the same gene, indicating that no DNA contamination, mispriming, and/or primer-dimer artifacts occurred in the experiments. When the saliva was assayed immediately after sample were collected, equal validation efficiencies (6 of 7 markers were validated) were obtained by both standard and DSTA procedures, in which 5 markers overlapped. After 10-week storage at ambient temperature, expressions of all 7 transcripts were still increased in the OSCC patients, and 4 markers were still validated by both procedures. Most markers validated by the DSTA method showed higher ROC-plot AUC values than those assayed by standard procedures, even after 10 weeks of ambient temperature storage, indicating that the DSTA method can confer enhanced performance for detection of oral cancer salivary biomarkers.

Example 2: Proteome Stabilization in Saliva

Materials and Methods
Sample Collection and Processing

This examples shows that the salivary proteome is stable for approximately two weeks at room temperature (RT) without degradation by adding ethanol to the samples.

Saliva samples were collected from 10 healthy subjects. None of the subjects had any history of malignancy, immunodeficiencies, autoimmune disorders, hepatitis, and/or HIV infection, and had a mean age of 35 years. Subjects were asked to refrain from eating, drinking or using oral hygiene products for at least 1 h prior to collection. After rinsing their mouths with water, 5 mL saliva was collected from each subject into a 50 mL Falcon tube. These saliva samples were filtered with a 0.45 μm PVDF membrane (Millipore, Billerica, Mass., USA) to remove cells and any debris. The flow through was collected. During the sample preparation, saliva samples were always kept on ice. FIG. 7 is the schematic diagram for the sample preparation.

Filtered saliva samples were then aliquoted into microcentrifuge tubes and stored at RT, 4° C. and −80° C., respectively, after the four different treatments described as following: (I) saliva samples with protease inhibitors were prepared, aliquoted and placed at RT and 4° C. for storage. All samples were made up with distilled water to keep the same volume. An aliquot saliva sample that had been stored at −80° C. with added protease inhibitors was used as positive control in all the experiments. Protease inhibitor stock solution was prepared by adding 1 Roche complete tablet (Roche Diagnostics GmbH, Roche Applied Science, Mannheim, Germany) into 1 mL distilled water. For every 1 mL saliva, 20 μL stock solution was added and briefly mixed by vortex. (II) Saliva amylase depletion was conducted according to a previous report (Deutsch et al. *Electrophoresis* 29:4150 (2008)). Briefly, saliva samples were eluted from starch column to deplete amylase specifically. (III) For protein denaturing experiments, saliva samples were either boiled at 95° C. for 10 min or by adding 20-time volumes absolute ethanol (Fisher Scientific, NJ, USA). Denatured samples were kept at RT for two weeks. The saliva proteins were then precipitated by centrifugation at 20,000 g for 20 min. (IV) For the non-denaturing method, every 20 μL absolute ethanol was added to 100 μL saliva. All the samples were made up to equal volume with distilled water. At different time points, 1 aliquot of saliva sample that has been kept at RT or 4° C. was moved into a −80° C. freezer and stored until further analysis.

Protein Concentration Measurement

The protein concentration of each saliva sample was measured by using the BCA Protein Assay Kit (Thermo Scientific Pierce, IL, USA). Equal volume of each sample was loaded into a 96 well plate in duplicates. The experiment was performed according to the manufacturer's instruction and the plate was read at 562 nm.

SDS-PAGE and Western Blot

Equal volume of each saliva sample was used for SDS-PAGE and western blot. For SDS-PAGE, the 10% Bis-Tris gel was run at 150V in MES SDS Running Buffer for 1 h. Pre-stained protein standard (Invitrogen, CA, USA) was used to track protein migration. The gel was then stained with simple blue (Invitrogen, CA, USA). For western blot Zhang et al, *PloS ONE* 5:e15573), saliva proteins were run and transferred to a PVDF membrane using the iBlot (Invitrogen, CA, USA). The membrane was incubated with the primary antibody (mouse monoclonal antibody to actin, Sigma-Aldrich, St. Louis, Mich., USA) and then incubated with the secondary antibody (anti-mouse IgG, peroxidase-linked species-specific whole antibody from sheep) according to manufacturer's instructions, for 1 h at RT. Finally, the membrane was washed and visualized using ECL Plus detection kit (GE Healthcare, WI, USA).

In-Gel Trypsin Digestion and NanoLC-MS/MS Analysis

In-gel trypsin digestion and mass spectrometry protein identification were the same as previously described (Xiao and Wong, *Bioinformation* 5:294 (2011). Briefly, each cut gel slice was destained, and in-gel tryptic digestion was carried out overnight at 37° C. Tryptic peptides resulting from the digestion were then extracted and loaded to LC-MS/MS (Eksige NanoLC-2D with Thermo LTQXL) for protein identification. Spect was collected and processed by Xcalibur software v3.3.0 (Thermo Scientific, Waltham, Mass.). Combined MS and MS/MS spectra were converted from RAW to mzXML (ReAdW version 4.3.1) and submitted for database search again Human Swissprot by using X!Tandem (version 2010.04.21). The parameters for searching were enzyme trypsin, 1 missed cleavage, fixed modifications of carbamidomethyl (C), variable modifications of oxidation (M), parent ion tolerance 4 Da and fragment mass tolerance: ±0.4 Da. The criteria of two peptides and log (E-value)<−10 were used for protein identification.

ELISA

The ELISA tests for β-actin (Total (β-actin Sandwich ELISA Kit, Cell Signaling Technology, Inc., MA, USA) and IL1β (Thermo Scientific Pierce, IL, USA) were performed according to the manufacturer's instructions. All saliva samples were diluted 2 times with sample diluents for IL1β and 10 times for β-actin.

Data Analysis

The Graphpad Prism (Version 5.01) was used for all data analysis. P value was calculated based on T test and p<0.05 was used as cutoff for significance. One-way ANOVA was run to determine whether the groups are actually different in the measured characteristic. The signal intensity of the western blot bands was quantified by using the Image J software (NIH, Bethesda, Md., USA).

Results

Protease inhibitors are usually added during sample collection to prevent proteolysis. This investigation also assessed protease cocktail and different temperature conditions on proteome stabilization, because they are known to greatly affect the rate proteolysis (Chevalier et al, *Clin. Proteomics* 3:13 (2007)). Amylase removal may increase the stability of other salivary proteins and eases the characterization of low abundant proteins (Hu et al, *Proteomics* 6:6326 (2006). Ethanol has been fully evaluated for the stabilization of protein (Gekko and Timasheff, *Biochemistry* 20:4677 (1981). All these methods were tested and evaluated for their efficiency in proteome stabilization.

Figure 8:
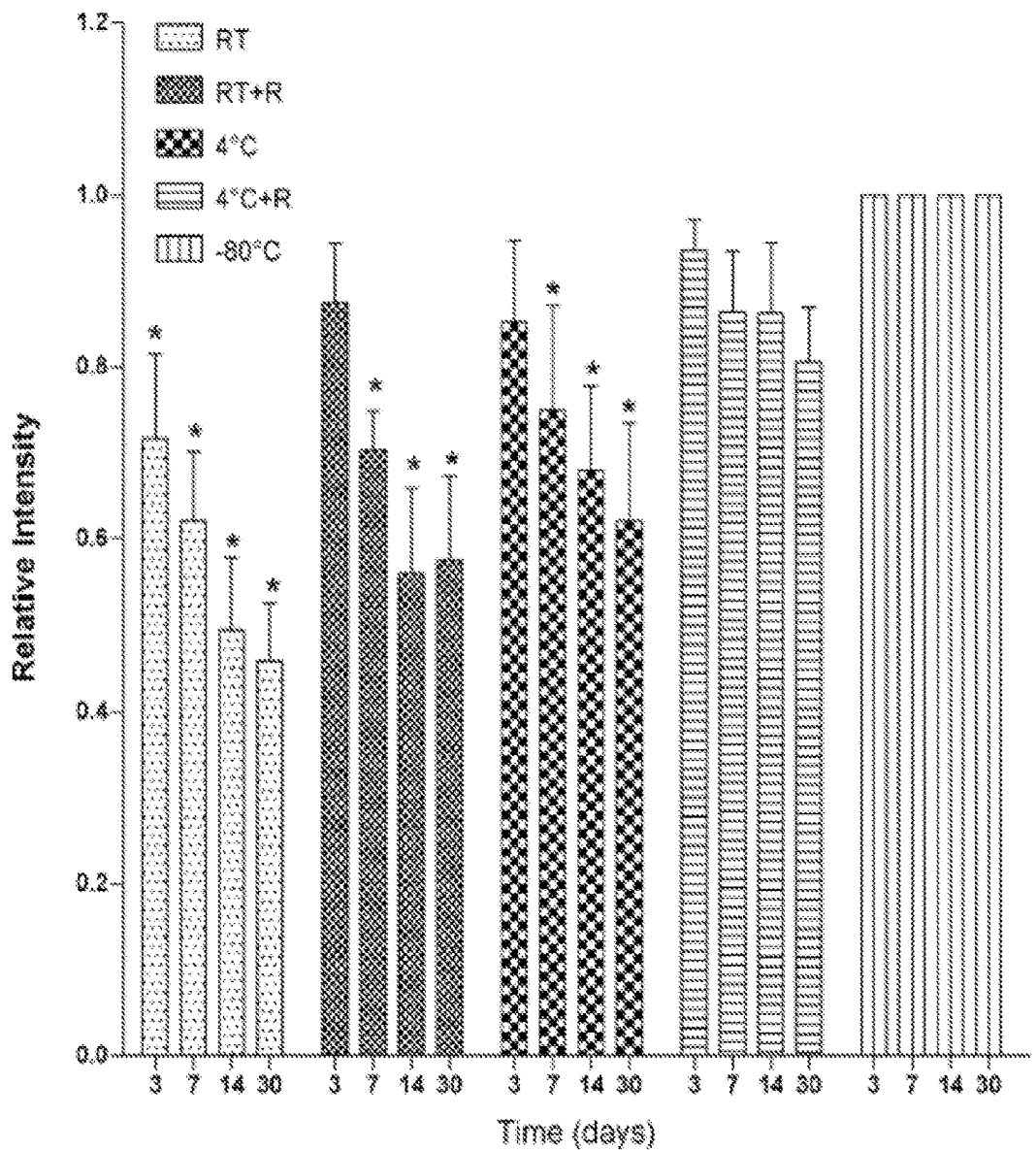
FIG. 8 illustrates ELISA analysis of saliva β-actin: RT+R: RT with protease inhibitors; 4° C.+R: 4 degree with protease inhibitors (n=5) (*: p<0.05).

The protein concentrations of saliva samples stored at RT and −80° C. were measured. The average total protein concentration the positive control was $1.19\pm0.15$ μg μL$^{-1}$ after stored at −80 for 30 days. Saliva stored at RT for 30 days was found to have total protein concentration of $0.76\pm0.21$ μg μL$^{-1}$, 36% less than that of positive control (p=0.0063, n=5), which demonstrated that salivary proteome had been significantly degraded.

β-actin in human saliva was degraded when the samples when stored at RT. As shown in FIG. 8, the stability of β-actin was systematically compared among different treatments by ELISA. There was significant degradation if saliva samples were stored at RT without any treatment. After 3 days, there was only 71.72±18% left when compared to positive control. If the saliva samples were kept a 4° C. with protease inhibitors, more than 85±12% of this protein could be detected in saliva and there was no significant change from positive control. In the saliva samples stored at RT with protease inhibitors, β-actin was found to be stable for only 3 days. When saliva samples were stored at 4° C. with protease inhibitor β-actin was found stable for about 1 month without significant degradation.

Figure 9:
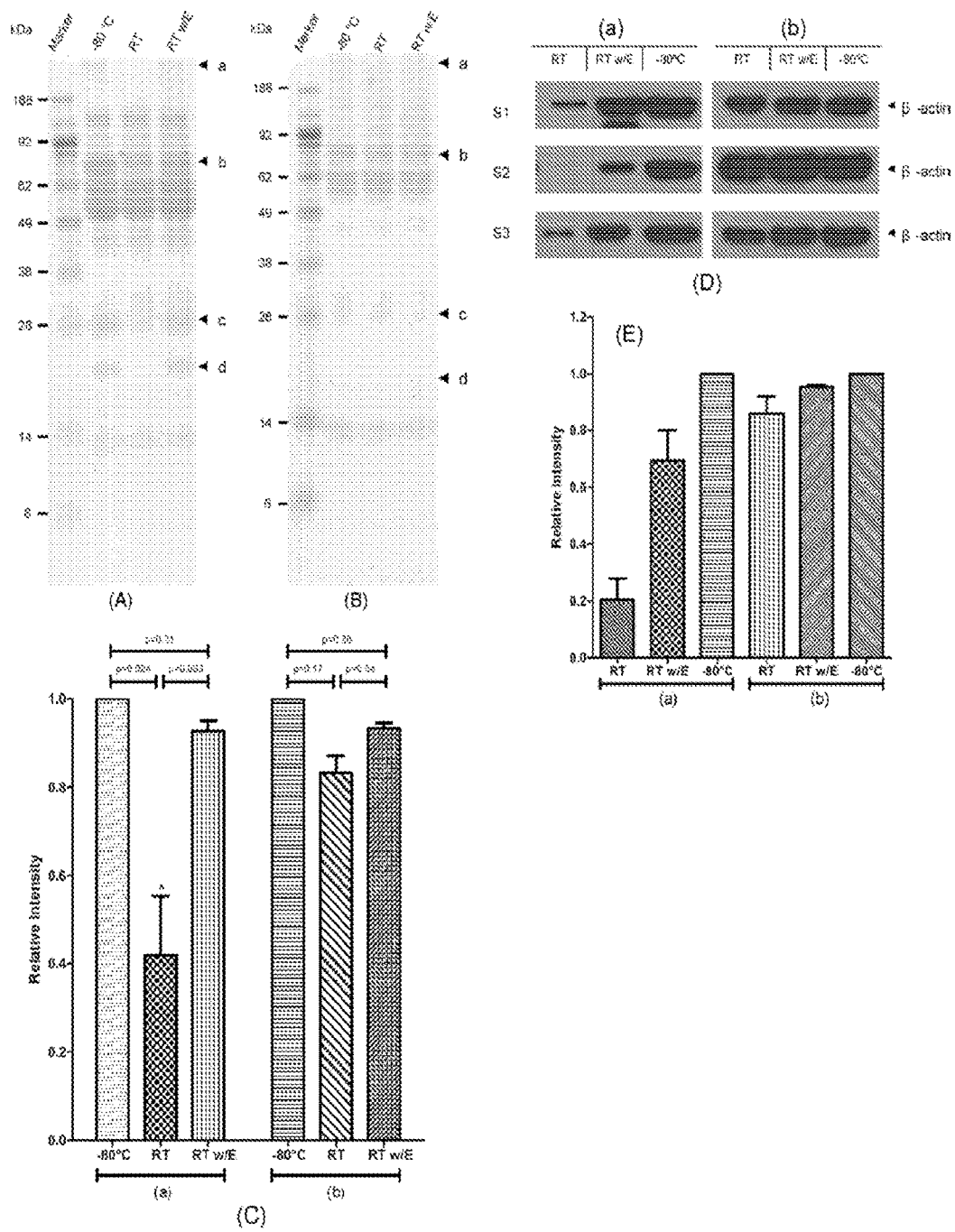
FIG. 9A-D illustrates SDS-Page for saliva proteins without (A) and with (B) amylase depletion, samples were stored for 3 days with corresponding treatment (C) Relative quantification of the labeled 4 bands (D) The western blot of β-actin after 7 days (E) The quantification data for the western blot in (D) (n=3). All quantification was normalized by the corresponding bands in the positive control. RT w/E: room temperature with adding 20% ethanol (a) without amylase depletion; (b) with amylase depletion.

Amylase is the most abundant protein in saliva and greatly affects the stability of other salivary proteins. After removing amylase from saliva, salivary proteins became more stable. The SDS-PAGE images of salivary proteins with and without amylase depletions are shown in FIGS. 9A and B. In FIG. 9A without amylase removal, the labeled bands a, b, c and d of lane RT were obviously weaker than that stored for 3 days at RT with 20% ethanol. All the 4 bands were quantified and then normalized to the corresponding positive control bands (FIG. 9C). The data demonstrated that there was significant difference between −80° C. and RT if no treatment was involved (p=0.024, n=4). When saliva samples were stored at RT with 20% ethanol, there was no significant change in comparison to the −80° C. samples (FIG. 9A) (p=0.31, n=4). In contrast, if amylase was removed from saliva, there was no significant degradation between either −80° C. and RT or RT with 20% ethanol (FIG. 9B) (p=0.17 and p=0.36, respectively, n=4). The western blot of β-actin in saliva after stored for 7 days also demonstrated that it became more stable after amylase removal (FIGS. 9D and E). If 20% ethanol was added, the stabilization efficiency for β-actin was better. In order to check what kind of proteins might have been protected by amylase removal, LC-MS/MS was run for the protein identification in the 4 bands of FIG. 9B lane RT. In the band a, three proteins were identified, including desmoplakin, deleted in malignant brain tumors 1 protein and syndecan-binding protein 2. In the band b, 7 proteins were found (mucin-7, tetra-peptide repeat homeobox protein 1, bactericidal/permeability-increasing protein-like 1, lactotransferrin, peroxisome proliferator-activated receptor gamma coactivator-related protein 1, alpha-2-macroglobulin, and polymeric immunoglobulin receptor). In the band c, several isoforms of immunoglobulin appeared, such as the heavy chain V-III, alpha-2, gamma-1, gamma-2 and gamma-4. Moreover, carbonic anhydrase 6, haptoglobin-related protein and cytoplasmic 1 actin were also identified. In the band d, 6 proteins were discovered. They were Ig lambda-1, Ig kappa, zymogen granule protein 16, short palate lung and nasal epithelium carcinoma-associated protein 2, Glyceraldehyde-3-phosphate dehydrogenase and L-lactate dehydrogenase.

Figure 10:
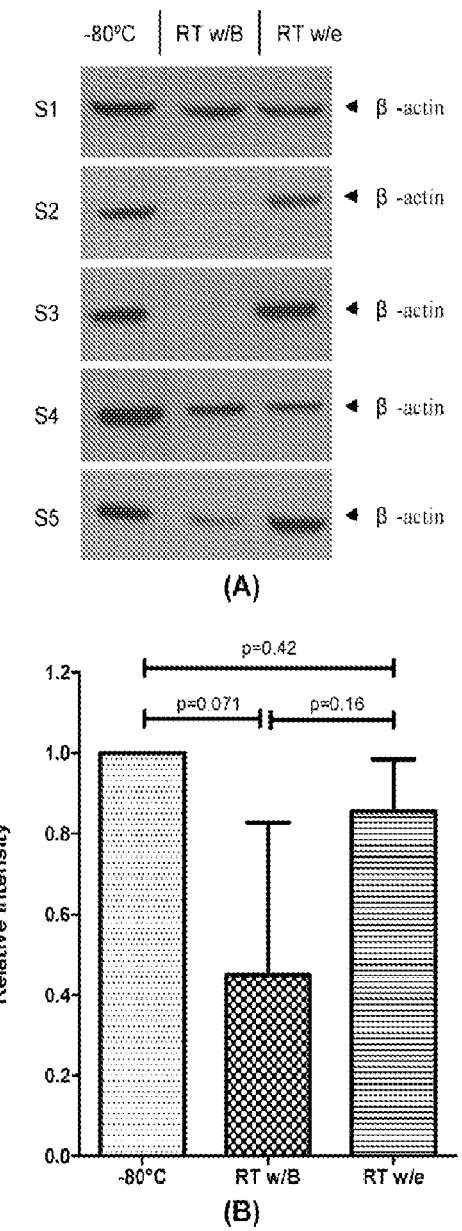
FIG. 10 illustrates Protein stabilization by denaturing. (A) Western blot of β-actin, RT w/B: RT with boiling, RT w/e: RT with 20-time volumes ethanol added (B) The quantification data for western blot in (A) (n=5).

We also explored the use of heat and ethanol denaturation to stabilize the salivary proteome. Saliva samples were treated either by boiling at 95° C. for 10 min or by precipitating with 20-time volumes ethanol. These saliva samples were then stored at RT. After two weeks, the β-actin in these samples were detected by western blot and compared with that of the positive control (FIG. 10A). There was no significant change after these denatured samples were kept at RT. Especially for ethanol precipitation, the stability of β-actin was very consistent in these five samples (FIG. 10B, p=0.42, n=5), while there was a relative large deviation for the boiled saliva samples (p=0.071, n=5).

By comparison of these methods that have been used to stabilize salivary proteins, 20% ethanol was chosen as an optimized approach to stabilize salivary proteome at RT. By adding ethanol to the samples and keeping them at RT for different time intervals, two proteins were measured by immunoassay, including β-actin and IL13.

The western blot of β-actin with different treatments was shown in FIG. 11A. Their corresponding quantifications were shown in FIG. 11B. The results showed that there was significant β-actin degradation at RT after day 3, 7 and 14 when compared to −80° C. By adding 20% ethanol to the saliva samples, protein degradation observed at RT were hindered with no significant difference found when compared to −80° C. (FIG. 11B) (p>0.05, n=8). However, after 30 days, significant degradation of β-actin was observed even though ethanol was added (p=0.0071, n=7).

Figure 12:
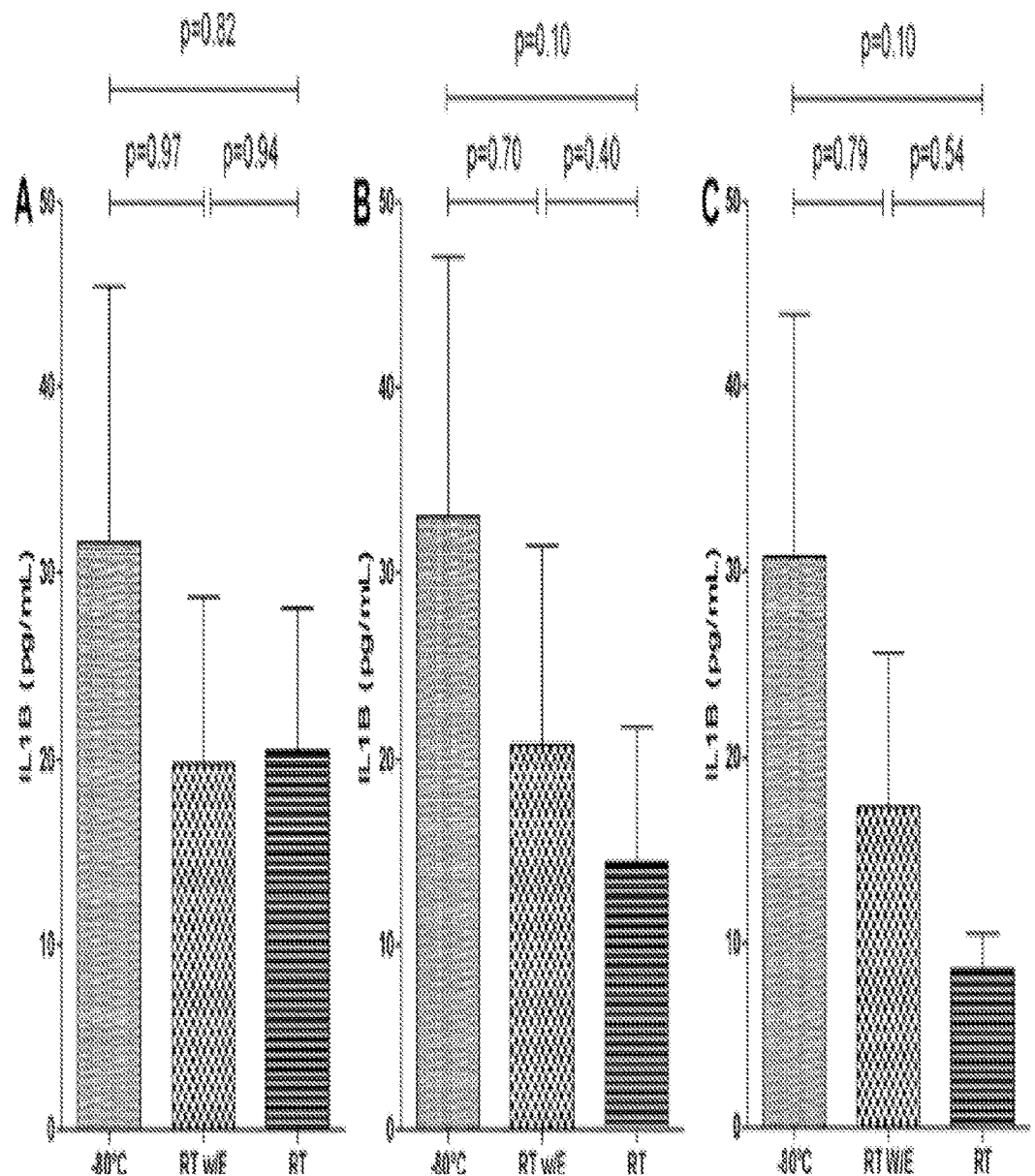
FIG. 12A-C illustrates ELISA of IL13 in saliva samples (n=10) at different conditions. (A) Stored for 7 days (B) Stored for 14 days (C) Stored for 30 days. RT w/E: room temperature with 20% ethanol added.

IL1β has been verified as an oral cancer salivary biomarker, which was tested by ELISA in this study. Although there was degradation with the prolonged time period, the data in FIG. 12 showed that IL1β was stable at RT even after 30 days (p>0.05). By adding 20% ethanol, the stability of this protein was increased (p>0.05, n=10).

Discussion

Besides protein, there are other types of analytes in human saliva, such as RNA (19), microRNA (Michael et al, *Oral Dis.* 16:34 (2010)), DNA (Jiang et al., *Clin. Cancer Res.* 11:2486 (2005)), metabolites (Sugimoto et al., *Metabolomics* 6:78 (2010)), cells (Xie et al., *Proteomics* 7:486 (2008)) and microbes (Ryu et al., *J. Oral Rehabil.* 37:194 (2010)). All these analytes may influence the quality and composition of salivary proteome. For example, there are different kinds of proteases in the saliva, which could digest diverse proteins. The protease inhibitor cocktail tablets used in this investigation were designed to inhibit a broad spectrum of serine, cysteine and metalloproteases as well as calpains (Chevalier et al., *Proteomics* 3:13 (2007)). Microbes may also generate some metabolites that can change the composition of human salivary proteome. RNA may interact with proteins and become stable (Palanisamy et al., *J. Dent. Res.* 87:772 (2008)). The storage temperature will also change the activity of different proteases, which will alter the stability of different proteins. By considering all these factors, salivary proteome is facing a huge risk of being digested or changed under different circumstances.

The efficiency of different methods was evaluated by testing selected protein targets. In order to properly stabilize salivary proteins, the activity of salivary proteases should be inhibited. Otherwise, as shown in FIG. 9A, salivary proteins will degrade quickly. In order to lower the metabolism of microbes, saliva sample should be kept at −80° C.

Protease inhibitors were added to hinder protein degradation because saliva samples without any treatment will be digested very quickly, although the salivary protein concentrations were significantly lower than the positive control after 30 days at RT. The data provided herein show that the addition of protease inhibitors and storage at 4° C. could effectively stabilize this protein for approximately two weeks. However, saliva samples could only be stabilized at RT for 3 days without significant change by adding protease inhibitors.

Upon amylase depletion, the salivary proteome became more stable. By removing amylase, salivary protein degradation at RT was not obvious when compared with that without amylase depletion (FIGS. 9A and B). In total, 24 proteins have been identified in the selected 4 gel bands, which might have been protected by amylase removal. Most of them have the molecular function of binding and catalytic activity. Amylase removal could greatly benefit the characterization of low abundant proteins (Hu et al., *Proteomics* 6:6326 (2006)). However, although this strategy is promising for saliva protein stabilization, there are several weaknesses for this method. Firstly, the saliva samples need additional treatment, which increased the complexity of sample collection. Secondly, the saliva samples are diluted 5-10 times after amylase depletion, which may affect the downstream analysis. Lastly, some saliva proteins may also be removed by using the starch column.

Figure 11:
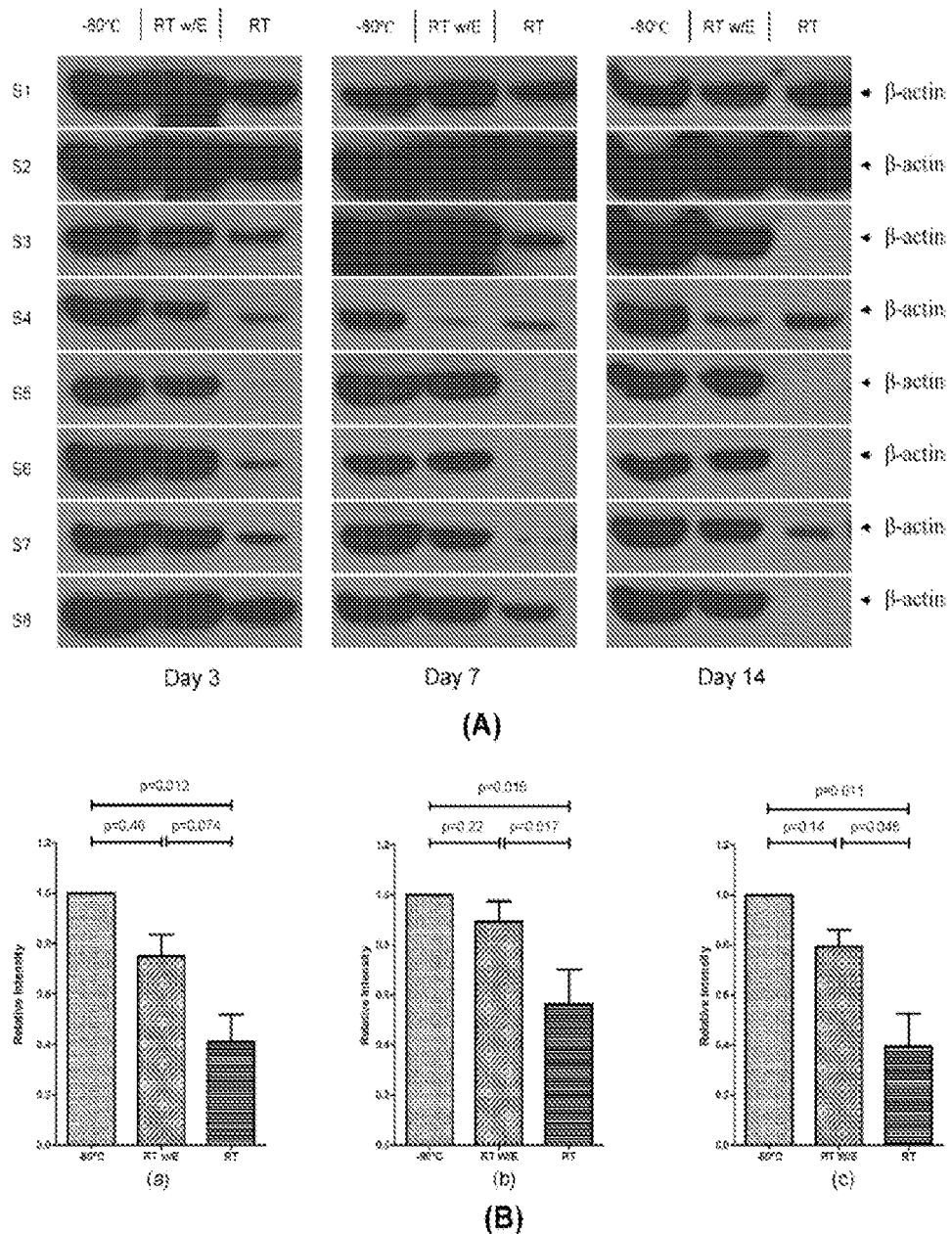
FIG. 11 illustrates western blot of β-actin (A) with and without adding ethanol at day 3, day 7 and day 14. The quantification data is shown in dot plot (B) (n=8). RT w/E: room temperature with 20% ethanol added.

Denaturing of proteins kills microbes and alters the protein structure. Both heat and organic solvents can stabilize proteins by changing their structure (Polson et al, *Anal. Technol. Biomed. Life Sci.* 785:263 (2003). Data provided herein showed that the denatured saliva samples could be stored at RT for two weeks without significant change when compared to the positive control. Nevertheless, in terms of clinical usage, these proteins are unsuitable for some analysis, such as structure-related analysis and assay, as well as immunoassays, such as ELISA. By lowering the added volume of ethanol to 20%, the proteins in saliva could still be stabilized at RT without significant degradation for at least two weeks (FIGS. 11 and 12).

Example 3: Saliva Collection, Processing, Stabilization, and Storage (SCPSS)

Subjects were asked to refrain from eating, drinking, smoking, and oral hygiene activities for at least 2 hours prior to collection. Whole unstimulated saliva was then collected using the Oasis saliva collector "Super●SAL" (FIG. 13) for about 10-15 min. The collected saliva was then processed for respective molecular constituent (DNA, Protein and RNA) stabilization and storage.

The collection tubes were pre-loaded with specific stabilizers for protein, RNA and DNA. All samples can be transported and stored at room temperature.
Isolation of Mammalian and Microbial DNA
An aliquot of whole saliva (1-2 ml) was dispensed into a microfuge tube. An equal volume of 2× lysis and DNA Stabilization Buffer (Oasis Diagnostics) were added and maintained at room temperature.
Isolation of RNA
For salivary RNA and proteins, the collected saliva is pushed through a barrel where there is a filtration unit (Millipore MGGF filter, 5 nm hydrophilic PVDF membrane) at the sample filtration end serving to remove cells, microbes and debris.

Half of the volume of the saliva filtrate is stored in a microfuge tube at room temperature for downstream applications including direct saliva transcriptome analysis. This sample was maintained at room temperature.
Isolation of Polypeptides
Half of the collected saliva filtrate is placed in a microfuge tube, an equal volume of 40% ethanol is added to the sample. This sample can be maintained at room temperature.

Example 4: Analysis of Protein and Nucleic Acid from Collected Saliva Samples

Subjects will be asked to refrain from eating, drinking, smoking, and oral hygiene activities for at least 2 hours prior to collection. Whole unstimulated saliva will then be collected using an apparatus for the collection of saliva comprising a sample collection pad, a receiving device, and a filter connected to the receiving device. The filter is a 5 nm hydrophilic membrane that filters out cells and microorganisms.

The filtered sample (1-2 ml) that is free from cells, microbes, and debris will be aliquoted into two microfuge collection tubes. The first tube will have a 20% ethanol solution and the second tube will be free of ethanol. All collection activities will be conducted at ambient temperatures.
Protein Analysis
The filtered sample collected in the first tube having a 20% ethanol solution will be stored at room temperature for up to two weeks for downstream applications.

The filtered sample for protein analysis will have the protein concentration measured, and the sample will be used for SDS-PAGE and western blot analyses. The saliva proteins will be run and transferred to a protein membrane. The membrane containing the protein will be incubated with primary antibody and then secondary antibody. In-gel trypsin digestion and mass spectrometry will then be used to identify extracellular saliva proteins.
RNA Analysis
The filtered sample collected in the second tube without ethanol will be stored at room temperature for up to ten weeks for downstream applications, including direct saliva transcriptome analysis. The filtered samples will then be treated with DNase. RT-qPCR will then be used to analyze mRNA expression levels of extracellular saliva mRNAs. The expression levels of the salivary transcripts will be detected using standard procedures of raw quantification cycle (Cq) values. Statistical comparison by ANOVA will be performed at a significance level of $P<0.05$ based on the Wilcoxon signed-rank test.

This example describes dual analysis of protein and nucleic acids collected from saliva samples by any person that is not required to be a specially trained technician. The samples will be collected and aliquoted for both protein and nucleic analysis, and subsequently stored at room temperature prior to analysis.

The examples set forth above are provided to give those of ordinary skill in the art a complete disclosure and description of how to make and use the embodiments of the compositions, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

What is claimed is:

1. A method for stabilizing nucleic acid and protein samples isolated from a saliva sample, the method comprising:
   a) collecting a saliva sample from a subject;
   b) filtering the saliva sample at ambient temperature to produce a filtered sample that is free of cells;
   c) collecting the filtered sample at ambient temperature into at least a first and a second receiving device;
   d) adding an alcohol solution to the first receiving device at ambient temperature to produce an alcohol-containing filtered sample to form a protein sample, with the proviso that alcohol is not added to the second receiving device to produce an alcohol-free filtered sample to form a nucleic acid sample; and
   e) storing the protein sample and the nucleic acid sample for at least 3 days at 25 degrees Celsius.

2. The method of claim 1, wherein the nucleic acid is DNA.

3. The method of claim 2, further comprising performing a polymerase chain reaction (PCR) analysis on the nucleic acid sample.

4. The method of claim 1, wherein the nucleic acid is RNA.

5. The method of claim 4, further comprising performing a RT-PCR analysis on the nucleic acid sample.

6. The method of claim 5, wherein the RT-PCR is reverse transcription quantitative real-time PCR (RT-qPCR).

7. The method of claim 1, wherein the alcohol solution comprises 20% ethanol.

8. The method of claim 1, further comprising performing a western blot, mass spectrometry protein identification, or ELISA analysis on the protein sample.

9. The method of claim 1, wherein the filtered samples are stored at ambient temperature for at least two weeks without more than 50% degradation of proteins or nucleic acids present in the filtered samples.

10. The method of claim 1, wherein the filtered samples are stored at ambient temperature for at least two weeks without more than 25% degradation of proteins or nucleic acids present in the filtered samples.

11. The method of claim 1, wherein the filtered samples are stored at ambient temperature for at least ten weeks without more than 50% degradation of proteins or nucleic acids present in the filtered samples.

12. The method of claim 1, further comprising the step of storing the filtered samples at ambient temperature for at least ten weeks without more than 25% degradation of proteins or nucleic acids present in the filtered samples.

13. The method of claim 1, wherein the alcohol solution comprises 15-25% ethanol.

14. The method of claim 1, wherein the alcohol solution comprises 5-35% ethanol.

15. The method of claim 1, wherein the filter is a hydrophilic membrane, and is selected from the group consisting of a 0.22 μm, 0.45 μm and 5.0 μm hydrophilic membrane.

16. The method of claim 15, wherein the filter is a 0.22 μm hydrophilic membrane.

17. A method for stabilizing nucleic acid and protein samples isolated from a saliva sample, the method comprising:
   a) collecting a saliva sample from a human subject;
   b) filtering the saliva sample at ambient temperature using a 0.22 μm to 5.0 μm hydrophilic membrane to produce a filtered sample that is free of cells;
   c) collecting the filtered sample at ambient temperature in a first and a second receiving device;
   d) adding an ethanol solution to the first receiving device at ambient temperature to produce an ethanol-containing filtered sample to form a protein sample, with the proviso that alcohol is not added to the second receiving device to produce an alcohol-free filtered sample to form a nucleic acid sample; and
   e) storing the protein sample and the nucleic acid sample for at least 3 days at 25 degrees Celsius.

18. The method of claim 17, wherein the protein sample is stabilized for at least 2 weeks when stored at 25 degrees Celsius.

19. The method of claim 17, wherein the nucleic acid sample is stabilized for at least 10 weeks when stored at 25 degrees Celsius.

20. The method of claim 17, further comprising the step of: f) performing an analysis on the filtered samples collected in the first and second receiving devices comprising one or more of: a protein analysis on the ethanol-containing filtered sample and a nucleic acid analysis on the alcohol-free filtered sample.

21. The method of claim 17, wherein the ethanol solution comprises 15-25% ethanol.

22. The method of claim 17, wherein the ethanol solution comprises 5-35% ethanol.

23. The method of claim 17, wherein the hydrophilic membrane is 0.22 μm.

* * * * *

```
                            SEQUENCE LISTING

<160> NUMBER OF SEQ ID NOS: 40

<210> SEQ ID NO 1
<211> LENGTH: 20
<212> TYPE: DNA
<213> ORGANISM: Artificial Sequence
<220> FEATURE:
<223> OTHER INFORMATION: GAPDH Outer Forward Primer

<400> SEQUENCE: 1
cctcaacgac cactttgtca                                                    20

<210> SEQ ID NO 2
<211> LENGTH: 18
<212> TYPE: DNA
<213> ORGANISM: Artificial Sequence
<220> FEATURE:
<223> OTHER INFORMATION: GAPDH Outer Reverse Primer

<400> SEQUENCE: 2
atgtgggcca tgaggtcc                                                      18

<210> SEQ ID NO 3
<211> LENGTH: 25
<212> TYPE: DNA
<213> ORGANISM: Artificial Sequence
<220> FEATURE:
<223> OTHER INFORMATION: GAPDH Inner Forward Primer

<400> SEQUENCE: 3
accactttgt caagctcaat ttcct                                              25

<210> SEQ ID NO 4
<211> LENGTH: 22
<212> TYPE: DNA
<213> ORGANISM: Artificial Sequence
<220> FEATURE:
<223> OTHER INFORMATION: GAPDH Inner Reverse Primer

<400> SEQUENCE: 4
caccctgttg ctgtagccaa at                                                 22

<210> SEQ ID NO 5
<211> LENGTH: 20
<212> TYPE: DNA
<213> ORGANISM: Artificial Sequence
<220> FEATURE:
<223> OTHER INFORMATION: ACTB Outer Forward Primer

<400> SEQUENCE: 5
gatcattgct cctcctgagc                                                    20

<210> SEQ ID NO 6
<211> LENGTH: 20
<212> TYPE: DNA
<213> ORGANISM: Artificial Sequence
<220> FEATURE:
<223> OTHER INFORMATION: ACTB Outer Reverse Primer

<400> SEQUENCE: 6
```
cggactcgtc atactcctgc                                         20

<210> SEQ ID NO 7
<211> LENGTH: 20
<212> TYPE: DNA
<213> ORGANISM: Artificial Sequence
<220> FEATURE:
<223> OTHER INFORMATION: ACTB Inner Forward Primer

<400> SEQUENCE: 7
ctcctgagcg caagtactcc                                         20

<210> SEQ ID NO 8
<211> LENGTH: 22
<212> TYPE: DNA
<213> ORGANISM: Artificial Sequence
<220> FEATURE:
<223> OTHER INFORMATION: ACTB Inner Reverse Primer

<400> SEQUENCE: 8
atactcctgc ttgctgatcc ac                                      22

<210> SEQ ID NO 9
<211> LENGTH: 20
<212> TYPE: DNA
<213> ORGANISM: Artificial Sequence
<220> FEATURE:
<223> OTHER INFORMATION: RPS9 Outer Forward Primer

<400> SEQUENCE: 9
atctcgtctc gaccaagagc                                         20

<210> SEQ ID NO 10
<211> LENGTH: 20
<212> TYPE: DNA
<213> ORGANISM: Artificial Sequence
<220> FEATURE:
<223> OTHER INFORMATION: RPS9 Outer Reverse Primer

<400> SEQUENCE: 10
tttgaccctc cagacctcac                                         20

<210> SEQ ID NO 11
<211> LENGTH: 21
<212> TYPE: DNA
<213> ORGANISM: Artificial Sequence
<220> FEATURE:
<223> OTHER INFORMATION: RPS9 Inner Forward Primer

<400> SEQUENCE: 11
cgaccaagag ctgaagctga t                                       21

<210> SEQ ID NO 12
<211> LENGTH: 20
<212> TYPE: DNA
<213> ORGANISM: Artificial Sequence
<220> FEATURE:
<223> OTHER INFORMATION: RPS9 Inner Reverse Primer

<400> SEQUENCE: 12
ccagacctca cgtttgttcc                                         20

<210> SEQ ID NO 13
<211> LENGTH: 20
<212> TYPE: DNA

```
<213> ORGANISM: Artificial Sequence
<220> FEATURE:
<223> OTHER INFORMATION: H3F3A Outer Forward Primer

<400> SEQUENCE: 13
agcgtctggt gcgagaaatt                                                    20

<210> SEQ ID NO 14
<211> LENGTH: 22
<212> TYPE: DNA
<213> ORGANISM: Artificial Sequence
<220> FEATURE:
<223> OTHER INFORMATION: H3F3A Outer Reverse Primer

<400> SEQUENCE: 14
gcacacaggt tggtgtcttc aa                                                 22

<210> SEQ ID NO 15
<211> LENGTH: 20
<212> TYPE: DNA
<213> ORGANISM: Artificial Sequence
<220> FEATURE:
<223> OTHER INFORMATION: H3F3A Inner Forward Primer

<400> SEQUENCE: 15
cgcttccaga gcgcagctat                                                    20

<210> SEQ ID NO 16
<211> LENGTH: 22
<212> TYPE: DNA
<213> ORGANISM: Artificial Sequence
<220> FEATURE:
<223> OTHER INFORMATION: H3F3A Inner Reverse Primer

<400> SEQUENCE: 16
tcttcaaaaa ggccaaccag at                                                 22

<210> SEQ ID NO 17
<211> LENGTH: 23
<212> TYPE: DNA
<213> ORGANISM: Artificial Sequence
<220> FEATURE:
<223> OTHER INFORMATION: IL1B Outer Forward Primer

<400> SEQUENCE: 17
gtacctgtcc tgcgtgttga aag                                                23

<210> SEQ ID NO 18
<211> LENGTH: 27
<212> TYPE: DNA
<213> ORGANISM: Artificial Sequence
<220> FEATURE:
<223> OTHER INFORMATION: IL1B Outer Reverse Primer

<400> SEQUENCE: 18
ttctatcttg ttgaagacaa atcgctt                                            27

<210> SEQ ID NO 19
<211> LENGTH: 25
<212> TYPE: DNA
<213> ORGANISM: Artificial Sequence
<220> FEATURE:
<223> OTHER INFORMATION: IL1B Inner Forward Primer

<400> SEQUENCE: 19
tgttgaaaga tgataagccc actct                                              25
```

<210> SEQ ID NO 20
<211> LENGTH: 24
<212> TYPE: DNA
<213> ORGANISM: Artificial Sequence
<220> FEATURE:
<223> OTHER INFORMATION: IL1B Inner Reverse Primer

<400> SEQUENCE: 20
caaatcgctt ttccatcttc ttct                                    24

<210> SEQ ID NO 21
<211> LENGTH: 25
<212> TYPE: DNA
<213> ORGANISM: Artificial Sequence
<220> FEATURE:
<223> OTHER INFORMATION: IL8 Outer Forward Primer

<400> SEQUENCE: 21
tttctgatgg aagagagctc tgtct                                   25

<210> SEQ ID NO 22
<211> LENGTH: 26
<212> TYPE: DNA
<213> ORGANISM: Artificial Sequence
<220> FEATURE:
<223> OTHER INFORMATION: IL8 Outer Reverse Primer

<400> SEQUENCE: 22
atcttcactg attcttggat accaca                                  26

<210> SEQ ID NO 23
<211> LENGTH: 20
<212> TYPE: DNA
<213> ORGANISM: Artificial Sequence
<220> FEATURE:
<223> OTHER INFORMATION: IL8 Inner Forward Primer

<400> SEQUENCE: 23
ccaaggaaaa ctgggtgcag                                         20

<210> SEQ ID NO 24
<211> LENGTH: 27
<212> TYPE: DNA
<213> ORGANISM: Artificial Sequence
<220> FEATURE:
<223> OTHER INFORMATION: IL8 Inner Reverse Primer

<400> SEQUENCE: 24
cttggatacc acagagaatg aattttt                                 27

<210> SEQ ID NO 25
<211> LENGTH: 17
<212> TYPE: DNA
<213> ORGANISM: Artificial Sequence
<220> FEATURE:
<223> OTHER INFORMATION: OAZ1 Outer Forward Primer

<400> SEQUENCE: 25
tgcgagccga ccatgtc                                            17

<210> SEQ ID NO 26
<211> LENGTH: 20
<212> TYPE: DNA
<213> ORGANISM: Artificial Sequence
<220> FEATURE:

<223> OTHER INFORMATION: OAZ1 Outer Reverse Primer

<400> SEQUENCE: 26
ccccggtctc acaatctcaa        20

<210> SEQ ID NO 27
<211> LENGTH: 24
<212> TYPE: DNA
<213> ORGANISM: Artificial Sequence
<220> FEATURE:
<223> OTHER INFORMATION: OAZ1 Inner Forward Primer

<400> SEQUENCE: 27
tcttcatttg cttccacaag aacc        24

<210> SEQ ID NO 28
<211> LENGTH: 21
<212> TYPE: DNA
<213> ORGANISM: Artificial Sequence
<220> FEATURE:
<223> OTHER INFORMATION: OAZ1 Inner Reverse Primer

<400> SEQUENCE: 28
tcaaagccca aaaagctgaa g        21

<210> SEQ ID NO 29
<211> LENGTH: 26
<212> TYPE: DNA
<213> ORGANISM: Artificial Sequence
<220> FEATURE:
<223> OTHER INFORMATION: SAT1 Outer Forward Primer

<400> SEQUENCE: 29
cgtgatgagt gattatagag gctttg        26

<210> SEQ ID NO 30
<211> LENGTH: 23
<212> TYPE: DNA
<213> ORGANISM: Artificial Sequence
<220> FEATURE:
<223> OTHER INFORMATION: SAT1 Outer Reverse Primer

<400> SEQUENCE: 30
ggttcattcc attctgctac caa        23

<210> SEQ ID NO 31
<211> LENGTH: 25
<212> TYPE: DNA
<213> ORGANISM: Artificial Sequence
<220> FEATURE:
<223> OTHER INFORMATION: SAT1 Inner Forward Primer

<400> SEQUENCE: 31
ttggcatagg atcagaaatt ctgaa        25

<210> SEQ ID NO 32
<211> LENGTH: 23
<212> TYPE: DNA
<213> ORGANISM: Artificial Sequence
<220> FEATURE:
<223> OTHER INFORMATION: SAT1 Inner Reverse Primer

<400> SEQUENCE: 32
tctgctacca agaagtgcat gct        23

<210> SEQ ID NO 33
<211> LENGTH: 21
<212> TYPE: DNA
<213> ORGANISM: Artificial Sequence
<220> FEATURE:
<223> OTHER INFORMATION: DUSP1 Outer Forward Primer

<400> SEQUENCE: 33
cctgtggagg acaaccacaa g                                             21

<210> SEQ ID NO 34
<211> LENGTH: 19
<212> TYPE: DNA
<213> ORGANISM: Artificial Sequence
<220> FEATURE:
<223> OTHER INFORMATION: DUSP1 Outer Reverse Primer

<400> SEQUENCE: 34
gcctggcagt ggacaaaca                                                19

<210> SEQ ID NO 35
<211> LENGTH: 22
<212> TYPE: DNA
<213> ORGANISM: Artificial Sequence
<220> FEATURE:
<223> OTHER INFORMATION: DUSP1 Inner Forward Primer

<400> SEQUENCE: 35
cagacatcag ctcctggttc aa                                            22

<210> SEQ ID NO 36
<211> LENGTH: 21
<212> TYPE: DNA
<213> ORGANISM: Artificial Sequence
<220> FEATURE:
<223> OTHER INFORMATION: DUSP1 Inner Reverse Primer

<400> SEQUENCE: 36
caaacaccct tcctccagca t                                             21

<210> SEQ ID NO 37
<211> LENGTH: 18
<212> TYPE: DNA
<213> ORGANISM: Artificial Sequence
<220> FEATURE:
<223> OTHER INFORMATION: S100P Outer Forward Primer

<400> SEQUENCE: 37
gcacgcagac cctgacca                                                 18

<210> SEQ ID NO 38
<211> LENGTH: 21
<212> TYPE: DNA
<213> ORGANISM: Artificial Sequence
<220> FEATURE:
<223> OTHER INFORMATION: S100P Outer Reverse Primer

<400> SEQUENCE: 38
cgtccaggtc cttgagcaat t                                             21

<210> SEQ ID NO 39
<211> LENGTH: 22
<212> TYPE: DNA
<213> ORGANISM: Artificial Sequence
<220> FEATURE:
<223> OTHER INFORMATION: S100P Inner Forward Primer

```
<400> SEQUENCE: 39
gctgatggag aaggagctac ca                                              22

<210> SEQ ID NO 40
<211> LENGTH: 22
<212> TYPE: DNA
<213> ORGANISM: Artificial Sequence
<220> FEATURE:
<223> OTHER INFORMATION: S100P Inner Reverse Primer

<400> SEQUENCE: 40
ttgagcaatt tatccacggc at                                              22
```